United States Patent
Winston et al.

(10) Patent No.: US 6,485,708 B1
(45) Date of Patent: *Nov. 26, 2002

(54) PRODUCTS AND METHODS FOR THE REMINERALIZATION AND PREVENTION OF DEMINERALIZATION OF TEETH

(75) Inventors: Anthony E. Winston, East Brunswick, NJ (US); Norman Usen, Marlboro, NJ (US)

(73) Assignee: Church & Dwight Co. Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/309,559

(22) Filed: May 13, 1999

(51) Int. Cl.⁷ .............................. A61K 7/16; A61K 7/18
(52) U.S. Cl. .............................. 424/52; 424/49; 424/57
(58) Field of Search ........................ 424/49–88

(56) References Cited

U.S. PATENT DOCUMENTS

| | | | |
|---|---|---|---|
| 3,679,360 A | | 7/1972 | Rubin et al. .................... 23/109 |
| 4,080,440 A | * | 3/1978 | DiGuilio et al. ............... 424/40 |
| 4,083,955 A | | 4/1978 | Grabenstetter ............... 424/49 |
| 4,097,588 A | | 6/1978 | Levine .......................... 424/52 |
| 4,097,935 A | | 7/1978 | Jarcho ............................ 3/1.9 |
| 4,177,258 A | | 12/1979 | Gaffar et al. .................. 424/52 |
| 4,183,915 A | | 1/1980 | Gaffar et al. .................. 424/52 |
| 4,348,381 A | | 9/1982 | Gaffar et al. .................. 424/52 |
| 4,397,837 A | * | 8/1983 | Raaf et al. ..................... 424/52 |
| 4,460,565 A | | 7/1984 | Weststrate et al. ............ 424/52 |
| 4,532,124 A | | 7/1985 | Pearce ........................... 424/52 |
| 4,556,561 A | | 12/1985 | Brown et al. ................ 424/151 |
| 4,606,912 A | | 8/1986 | Rudy et al. .................... 424/52 |
| 4,610,873 A | | 9/1986 | Rudy et al. .................... 424/52 |
| 5,037,639 A | | 8/1991 | Tung ............................. 424/57 |
| 5,145,668 A | | 9/1992 | Chow et al. ................... 424/52 |
| 5,268,167 A | | 12/1993 | Tung ............................. 424/52 |
| 5,427,768 A | | 6/1995 | Tung ............................. 424/52 |
| 5,437,857 A | | 8/1995 | Tung ............................. 424/52 |
| 5,460,803 A | | 10/1995 | Tung ............................. 424/57 |
| 5,571,502 A | * | 11/1996 | Winston et al. ............... 424/52 |
| 5,603,922 A | * | 2/1997 | Winston et al. ............... 424/49 |
| 5,605,675 A | * | 2/1997 | Usen et al. .................... 424/49 |
| 5,605,677 A | | 2/1997 | Schumann et al. ............ 424/52 |
| 5,614,175 A | * | 3/1997 | Winston et al. ............... 424/52 |
| 5,628,429 A | * | 5/1997 | Usen et al. ..................... 222/1 |
| 5,645,853 A | * | 7/1997 | Winston et al. ............. 424/440 |
| 5,817,296 A | * | 10/1998 | Winston et al. ............... 424/49 |
| 5,833,957 A | | 11/1998 | Winston et al. ............... 424/49 |
| 5,858,333 A | * | 1/1999 | Winston et al. ............... 424/57 |
| 5,860,565 A | * | 1/1999 | Winston et al. ................. 222/1 |
| 5,866,102 A | * | 2/1999 | Winston et al. ............... 424/52 |
| 5,895,641 A | * | 4/1999 | Usen et al. .................... 424/52 |
| 5,958,380 A | * | 9/1999 | Winston et al. ............... 424/48 |
| 6,120,754 A | * | 9/2000 | Lee et al. ...................... 424/49 |
| 6,159,448 A | * | 12/2000 | Winston et al. ............... 424/52 |
| 6,159,449 A | * | 12/2000 | Winston et al. ............... 424/52 |

OTHER PUBLICATIONS

U.S.S.N. 08/722,457, filed Sep. 27, 1996.

* cited by examiner

Primary Examiner—Shep K. Rose
(74) Attorney, Agent, or Firm—Stephen B. Shear

(57) ABSTRACT

Improved one-part and two-part liquid products such as, e.g., mouthwashes, mouthrinses, toothpastes, gels and the like, for remineralizing subsurface lesions and/or mineralizing exposed dentin tubules in teeth contain a cationic component, an anionic component and a separating means for separating the cationic and anionic components. The anionic component contains water-soluble phosphate and fluoride salts, while the cationic component contains at least one partially water-soluble calcium salt and preferably at least one water-soluble salt of a divalent metal other than calcium. The tooth is treated with a mixed aqueous composition formed by mixing the cationic and anionic components with water and/or saliva. The mixed aqueous composition has a pH of from about 4.0 to about 10.0 and, in addition to dissolved calcium cations and dissolved phosphate and fluoride anions, contains a quantity of undissolved calcium salt. The use of the partially water-soluble calcium salt delays precipitation of the cations and anions in the aqueous composition until after the ions have diffused through the tooth surface to the subsurface and/or dentin so as to effect remineralization and/or mineralization, respectively.

44 Claims, No Drawings

PRODUCTS AND METHODS FOR THE REMINERALIZATION AND PREVENTION OF DEMINERALIZATION OF TEETH

BACKGROUND OF THE INVENTION

This invention relates to improved products and methods for remineralizing subsurface lesions in teeth and for mineralizing exposed tubules in dentin so as to prevent demineralization thereof. More particularly, this invention relates to liquid dentifrice products containing cationic and anionic salts having different solubilities in water and to methods of using such products to remineralize subsurface lesions and/or to mineralize exposed dentin tubules.

The primary component of the enamel and dentin in teeth is calcium phosphate in the form of calcium hydroxyapatite. While highly insoluble at normal oral pHs, the calcium phosphate in the teeth tends to be relatively soluble in acidic media. Consequently, carious lesions can form in the subsurface of a tooth when such tooth is exposed to acids formed from the glycolysis of sugars caused by various oral bacteria.

Because saliva is supersaturated with respect to calcium and phosphate ions, saliva helps protect teeth against demineralization and can slowly remineralize teeth which have become demineralized by acids. It is well known that fluoride ions can enhance the natural remineralization process and this is one of the accepted mechanisms by which fluoride toothpastes and rinses protect against caries. However, the efficacy of fluoride-containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of saliva, the addition of higher levels of dissolved calcium and phosphate ions is not easily accomplished.

Remineralization of dental enamel has been carried out experimentally, both in vivo and in vitro. Some studies have concentrated on the remineralizing properties of saliva and of synthetic solutions supersaturated with respect to hydroxyapatite. Such studies comprise the subject matter of U.S. Pat. No. 3,679,360 (Rubin) and U.S. Pat. No. 4,097,935 (Jarcho).

Generally, the supersaturated solutions or slurries used in the aforementioned Rubin and Jarcho patents for remineralization experiments have been prepared from a single form of calcium phosphate. When a carious lesion is flooded with one of these supersaturated solutions, the calcium and phosphate ions in the form of precipitated hydroxyapatite remineralize the lesion. However, use of these solutions is impractical for several reasons. First, the amount of calcium and phosphate ions available for remineralization in these supersaturated solutions is too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because such solutions cannot maintain their supersaturated state. When the hydroxyapatite precipitates out to the point where the solution is no longer supersaturated, new supersaturated solution must be introduced or the remineralization process stops.

Another problem with single calcium phosphate slurries is that as the hydroxyapatite precipitates out of solution, the pH of the solution changes. Unless the old solution is removed from contact with the tooth material, the solution may become too acidic or alkaline and may damage the dental tissue.

U.S. Pat. No. 4,080,440 (Digiulio et al) discloses a metastable solution of calcium and phosphate ions at a low pH (between 2.5 and 4.0) under which conditions the solubility of calcium phosphate salts is high. After penetration of the solution into demineralized enamel, remineralization results from the precipitation of calcium phosphate salts when the pH rises. Fluoride ions can be included in the metastable solution. A significant disadvantage of the use of metastable solutions is that the relatively low pH might demineralize the dental enamel and/or injure other tissue.

U.S. Pat. Nos. 4,177,258, 4,183,915 and 4,348,381 (Gaffar et al) disclose a remineralizing solution containing supersaturated concentrations of calcium ions, phosphate ions and a fluoride source stabilized by the presence of an antinucleating agent such as diamine tetramethylenephosphonic acid, ethylenediamine tetramethylenephosphonic acid and 2-phosphonobutane-tricarboxylic acid-1,2,4, or the water-soluble salts thereof. This solution is preferably adjusted to the neutral pH range where the solution is alleged to most effectively remineralize subsurface lesions. Even though the antinucleating agent would be expected to stabilize the solution, equilibrium of the supersaturated concentrations is still found difficult to maintain and avoid precipitation of hydroxyapatite and changes in the pH of the solution.

U.S. Pat. No. 4,083,955 (Grabenstetter et al) and U.S. Pat. No. 4,397,837 (Raaf et al) disclose a process for remineralizing demineralized enamel by the consecutive treatment of tooth surfaces with separate solutions containing calcium ions and phosphate ions. In this process, fluoride ions may be present in the phosphate solutions. It is immaterial which ionic solution is used to treat the teeth first. By sequentially applying calcium and phosphate ions to the tooth surface, high concentrations of the ions are able to penetrate into lesions in solution form, where the ions precipitate as a calcium phosphate salt when ions from the second treatment solution diffuse in. While apparently successful, this method involves the inconvenience of a plurality of sequential applications, which can also be time consuming.

U.S. Pat. No. 4,606,912 (Rudy et al.) teaches a method of making a clear aqueous mouthwash solution capable of remineralizing lesions in teeth by forming an aqueous solution containing a source of calcium ions and a chelating agent for calcium ions, causing the chelation of at least 50% of the calcium ions and subsequently adding a source of phosphate ions to the aqueous solution. Here too, while somewhat effective, the addition and necessary control of the amount of chelating agent makes the concept impractical.

Another problem with known remineralization techniques is that the remineralization may stop before the lesion is completely remineralized due to build-up of the remineralized tooth material in or on the outer layer of the tooth's surface. This build-up occurs when the rate of remineralization is too fast and prevents the diffusion of the mineral into the deeper regions of the lesion, thus thwarting the full remineralization of the tooth.

U.S. Pat. Nos. 5,037,639; 5,268,167; 5,437,857; 5,427,768; and 5,460,803 (all to Tung) involve the use of amorphous calcium compounds such as amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. The compounds are claimed to have high solubilities, fast formation rates and fast conversion rates (to apatite).

Remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystallize to the less soluble apatite form in the lesion and reform the tooth. However, under conditions where amorphous calcium phosphate compounds are stable, the quantity of calcium and phosphate released is relatively low and, therefore, remineralization is slower than desirable.

The aforementioned patents to Tung also teach the use of two-part solutions wherein a first part contains phosphate salt(s) and a second part contains calcium salt(s), wherein either the first part or the second part further contains carbonate salt(s). In addition, the Tung patents teach solutions formed by dissolving in water a solid powder containing calcium salt(s), phosphate salt(s), and carbonate salt(s). These solutions are then applied to dental tissue. The Tung patents further teach the use of non-carbonated solid powders containing mixtures of calcium salts and phosphate salts which can be applied directly to the tooth or dispersed in gel, chewing gum, or other non-aqueous mediums such as toothpaste which is placed in contact with the tooth. The patents teach that these powders are easily dissolved in saliva and then reprecipitated as an amorphous calcium phosphate compound. However, the Tung patents do not disclose the pHs of aqueous solutions formed from the non-carbonated solid powder.

Effective remineralizing/mineralizing products and methods are continually desired which do not require the presence of carbonate salts to achieve stability, remineralization and/or mineralization. It is also continually desirable to provide remineralizing/mineralizing products and methods which directly form hydroxyapatite at the subsurface of the tooth rather than first forming an amorphous calcium phosphate as an intermediate. In addition, it is continually desirable to provide a remineralization product in the form of a one-part, stable remineralizing composition which is not negatively affected by a rise in pH or temperatures or which can efficiently remineralize teeth. Finally, there is a continual need for a method of remineralizing dental enamel which employs a stable, one-part remineralizing product which does not require excessive amounts of calcium and phosphate salts or inordinately long, frequent or sequential exposure times.

Remineralizing/mineralizing one-part and two-part products which overcome many of the aforementioned problems are disclosed in copending, commonly assigned U.S. Pat. Nos. 5,603,922, 5,833,957, 5,605,675, 5,895,641, 5,645,853, 5,571,502, 5,614,175, 5,866,102, 5,817,296 and 5,858,333.

Application Ser. No. 08/512,473 discloses one-part and two-part products and methods of using same to remineralize subsurface lesions. The one-part and two-part products contain at least one water-soluble calcium salt, at least one water-soluble divalent metal salt wherein the divalent metal is other than calcium and at least one water-soluble phosphate salt. In the two-part products, the calcium and divalent metal salts are disposed in a first discrete component, and the phosphate salt(s) is disposed in a second discrete component. The two-part product may further contain a dispensing means for allowing the first and second components to be simultaneously dispensed from the product so as to permit the dispensed first and second components to simultaneously contact the tooth or teeth being treated. The aqueous solution formed by mixing the salts used in the one-part and two-part products has a pH of from about 4.0 to about 7.0.

U.S. Pat. Nos. 5,605,675 and 5,895,641 discloses a two-part product and method of using same for remineralizing dental enamel, wherein the product contains a first discrete component containing at least one water-soluble calcium salt and a second discrete component containing at least one water-soluble phosphate salt and at least one water-soluble fluoride salt. The product may further contain a means for allowing the first and second components to be simultaneously dispensed from the product. The first and second components of the product each have a pH such that when the two components are mixed to form an aqueous mixed solution, the solution has a pH of from about 4.5 and 10.0.

U.S. Pat. No. 5,645,853 is directed to a chewing gum product and method of using same for remineralizing subsurface lesions in teeth, wherein the product contains a water-soluble cationic portion composed of at least one water-soluble calcium salt and at least one water-soluble, non-toxic divalent metal salt wherein the divalent metal is other than calcium; a water-soluble anionic portion containing at least one water-soluble phosphate salt; and a gum base. The anionic and cationic portions are disposed in the product such that chewing of the product in the presence of water and/or saliva causes the anionic and cationic portions to be simultaneously released into the water and/or saliva so as to form a mixed aqueous solution therewith. The anionic and cationic portions each have a pH when dissolved in water and/or saliva such that the mixed aqueous solution has a pH of from about 4.0 to 7.0.

U.S. Pat. Nos. 5,571,502, 5,614,175 and 5,866,102 are directed to one-part, non-aqueous products and methods of using same for remineralizing subsurface lesions, wherein the products contain at least one water-soluble calcium salt; at least one water-soluble phosphate salt; either a stabilizer or a hydrophilic, non-aqueous, water-soluble vehicle; and, optionally, at least one water-soluble fluoride salt. When the components are mixed with water or saliva to form an aqueous mixed solution, the solution has a pH of from about 4.5 to about 10.0.

In the one-part and two-part products disclosed in the foregoing applications, the cationic and anionic components are kept separate from one another until use of the product. In addition, the cations and anions are delivered simultaneously to the surface of the tooth being treated. These factors, along with the pH of the aqueous solution and the use in some cases of at least one water-soluble divalent metal salt, are helpful to allowing the cations and anions to have ample time to diffuse through the surface of the tooth to the subsurface before undergoing precipitation.

For mineralization or remineralization of enamel or dentin to occur, the concentration of calcium and phosphate ions in saliva must be above the concentration required to saturate the solution with respect to the formation of calcium hydroxyapatite, octacalcium phosphate, dicalcium phosphate dihydrate, or other form of insoluble calcium phosphate. At pHs above about 6.5, these requirements are met by the levels of calcium and phosphate in normal human saliva. However, because the concentration of calcium and phosphate ions in normal human saliva is only modest, even at pHs above 6.5, the rate of mineralization produced by normal saliva is very slow even when fluoride is present to catalyze the process. When the pH is above about 7, raising the concentration of calcium and phosphate ions much beyond that normally present in saliva does not, however, significantly increase remineralization. Because of the high insolubility of calcium phosphate salts above pHs of about 7, excessively rapid precipitation occurs which does not allow time for the ions to penetrate the tooth.

At pHs below about 7, significant remineralization will occur only if the concentration of calcium and phosphate ions in the saliva is above the concentration required to saturate the solution with respect to the formation of dicalcium phosphate dihydrate. Under these pH conditions, it has been demonstrated that remineralization can be accelerated by increasing the degree of supersaturation in saliva. Inasmuch as the solubility of dicalcium phosphate increases with decreasing pH, it has been found that when lesions are remineralized with solutions having a pH in the range of 4.5 to 7.0 and containing supersaturated quantities of calcium and phosphate ions, the optimum concentration of calcium ions needed to maximize the process increases with decreasing pH. Below a pH of about 4.0, dicalcium phosphate dihydrate becomes the stable precipitating species from supersaturated solutions. Under these pH conditions, it takes very high levels of calcium and phosphate to saturate the solutions. Under such conditions, there is a real danger with fairly high concentrations of calcium and phosphate hat the solution will be undersaturated and demineralization of the teeth being treated will occur.

It has also been found that the simultaneous provision of very high calcium and phosphate ion concentrations can result in premature precipitation of the calcium salt before the ions can penetrate the tooth or premature precipitation so as to block the entrances of the pores in tooth enamel and dentin and thereby prevent further remineralization.

Thus, a problem apparently exists in that to control untimely precipitation, the concentration of either the dissolved calcium ions or the dissolved phosphate ions needs to be limited. This in turn would be expected to disadvantageously limit the maximum rate of mineralization or remineralization which could be accomplished.

In addition, the use of very high calcium and fluoride ion concentrations can result in premature precipitation of the fluoride ions before these ions can penetrate the tooth. As mentioned previously herein, fluoride ions can enhance the natural remineralization process. However, sufficient levels of fluoride ions are generally required to be present. Calcium cations and fluoride anions precipitate to form calcium fluoride, a salt which is sparingly soluble in water. The formation of calcium fluoride is undesirable since it reduces the amount of free fluoride anions available for use in the remineralization process. Thus, it is desirable to provide a remineralizing product wherein the solution used to treat the teeth contains sufficient levels of dissolved fluoride anions to enhance the remineralization of the subsurface lesions.

Although the remineralization products disclosed in the aforementioned copending, commonly assigned patent applications are stable, it is continually desirable to provide alternative products which minimize the risk of premature precipitation of the cations and anions, particularly of the fluoride anions.

Accordingly, it is a primary object of this invention to provide products and methods for the remineralization and the prevention of demineralization of human teeth, wherein the products and methods are capable of effectively incorporating calcium ions, phosphate ions and fluoride ions into the subsurface of a tooth.

It is a further object of this invention to provide products and methods for the remineralization and the prevention of demineralization of human teeth, wherein the precipitation of the calcium, phosphate and fluoride ions is substantially avoided prior to diffusion of the ions into the subsurface of the tooth without reducing the rate of remineralization at the subsurface of the tooth.

It is another object of this invention to provide products and methods for the remineralization and the prevention of demineralization of human teeth, which do not require excessive amounts of solution or inordinately long or frequent exposure times.

It is still another object of the present invention to provide products for the remineralization and the prevention of demineralization of human teeth, wherein the products are easily usable by the consumer and do not differ significantly, in flavor or appearance, from customary dental cosmetics.

It is yet another object of this invention to provide an improved product and a method of preparing such product, wherein the product is maintainable in a single container, substrate or matrix and is capable of remineralizing lesions in the teeth and mineralizing normal teeth to prevent cariogenic lesions from forming therein.

It is a further object of this invention to provide remineralizing/mineralizing products and methods which can directly form hydroxyapatite in the subsurface of a tooth subsurface without first forming an amorphous calcium phosphate as an intermediate.

It is another object of this invention to provide two-part remineralizing/mineralizing products and methods of using same, wherein the products contain calcium salt(s) in a first part and phosphate salt(s) in a second part separate from the first part prior to introduction of the product into the oral cavity but wherein the product will simultaneously dispense the first and second parts from the product for use in the oral cavity.

Yet another object of the present invention is to provide products having the characteristics set forth in the foregoing objects and which are in the form of a toothpaste, gel, professional gel, cream, mouthwash, mouth rinse, and the like.

A further object of the present invention is to provide remineralization/mineralization methods using products having the characteristics set forth in the preceding objects.

It is yet another object of the present invention to provide an improved product and method having the characteristics set forth in the preceding objects wherein the active ingredient in the product is fluoride.

These and other objects which are achieved according to the present invention can be readily discerned from the following description.

SUMMARY OF THE INVENTION

The present invention provides effective remineralizing/mineralizing liquid products and methods of using same which overcome the aforementioned problems and achieve the foregoing objects.

Specifically, the present invention provides liquid products for remineralizing subsurface lesions and/or for mineralizing exposed dentin tubules in teeth, containing:

(a) a cationic component containing at least one partially water-soluble calcium salt;

(b) an anionic component containing at least one water-soluble phosphate salt and at least one water-soluble fluoride salt; and (c) a separating means disposed to separate components (a) and (b), wherein components (a) and (b) have a pH in water such that a mixed aqueous composition formed by mixing components (a) and (b) with water and/or saliva has a pH of from about 4.0 to about 10.0;

further wherein the product contains an amount of the calcium salt such that in the mixed aqueous composition a first portion of the calcium salt exists as dissolved calcium cations and a second portion of the calcium salt exists as undissolved calcium salt, the aqueous composition further containing phosphate anions released by the phosphate salt and fluoride anions released by the fluoride salt.

In the present invention, when the mixed aqueous composition is applied to a tooth (or teeth), the calcium cations and the phosphate and fluoride anions in the aqueous composition do not immediately precipitate but rather first diffuse through the surface of the tooth to the subsurface and/or dentin thereof, where the ions then combine to form an insoluble precipitate on the demineralized subsurface lesion(s) and/or on the exposed dentin tubule(s).

This invention is based on the discovery that such delayed precipitation of the calcium cations and the phosphate and fluoride anions until such ions have diffused through the tooth surface to the subsurface and/or dentin can be achieved by using in the cationic component at least one calcium salt having partial water-solubility at a pH of from about 4.0 to about 10.0. With the use of the partially water-soluble calcium salt(s) in the cationic component of the products of this invention, the calcium cations and the phosphate and fluoride anions in the mixed aqueous composition used to treat the tooth are able to remain soluble for the period of time sufficient to allow the cations and anions to diffuse through the surface of the tooth to the subsurface and/or dentin thereof, where, as stated above, the ions react to form an insoluble precipitate on the demineralized lesion(s) and/or exposed tubule(s).

This invention is also based on the discovery that the use of at least one partially water-soluble calcium salt in the products of this invention allows a greater level of free fluoride anions to be available for absorption by the tooth being treated than would be available when water-soluble calcium salts are used instead.

Thus, an important advantage of using the partially water-soluble calcium salt(s) in the present invention is that at any point in time the low concentration of calcium cations does not insolubilize either the phosphate anions or the fluoride anions, the cations and anions both being used in the remineralization and/or mineralization process.

Another advantage resulting from the use of the partially water-soluble calcium salt(s) in the present invention is that high concentrations of the undissolved calcium salt can be added to the dentifrice formulation without the danger of excessive concentrations of calcium cations being released at any one time to the saliva.

A further advantage resulting from the use of the partially water-soluble calcium salt(s) in the present invention is that, as the calcium cations in the mixed aqueous composition are used up (i.e., precipitated), the undissolved calcium salt can release additional calcium cations to the composition so as to maintain the rate of the remineralization and/or mineralization process.

Another particularly important advantage of using the partially water-soluble calcium salt(s) in the present invention is that, in the aqueous composition used to treat the teeth, the calcium salt(s) releases an amount of calcium cations sufficient to promote remineralization but insufficient to precipitate the fluoride. Thus, the maximum level of fluoride anions remains available for absorption by the tooth during application of the composition thereto.

Thus, the use of the partially water-soluble calcium salt(s) in the present invention provides a practical way to ensure close to optimum levels of calcium cations throughout the remineralization and/or mineralization process.

As stated hereinabove, the products of this invention remineralize and/or mineralize teeth using combinations of partially water-soluble calcium salts, water-soluble phosphate salts and fluoridating agents. Fluoride itself is a known remineralizing agent. The provision of calcium and phosphate salts in this invention serves to enhance the efficacy of the fluoride. Because of the short periods of exposure during brushing with toothpastes or rinsing with mouth rinses, it is believed that significant remineralization will not occur with these products in the absence of an active fluoride.

The products of the present invention provide substantially improved remineralization and mineralization as compared with the prior art products discussed hereinabove.

In addition, the methods of the present invention overcome the disadvantages of the prior art methods discussed hereinabove in that the methods of this invention effect subsurface remineralization rather than surface remineralization. Since dental caries begins as a subsurface demineralization of the dental enamel, subsurface remineralization arrests and repairs the carious lesion before any permanent structural damage to the tooth occurs.

Furthermore, the methods of the present invention do not require preparation of the enamel surface, capping of the tooth, or removal of decay products.

In addition, consumers may conveniently practice the methods of the present invention without substantially changing their dental care habits.

DETAILED DESCRIPTION OF THE INVENTION

As stated hereinabove, the present invention provides liquid products and methods of using same to remineralize subsurface lesions and/or mineralize exposed dentin tubules in teeth.

As used herein, the term "liquid" refers to a material having a consistency like that of a solution, a concentrate, a paste, a gel, a cream or the like.

The products of this invention are composed of a cationic component, an anionic component, and a separating means for separating the cationic and anionic components. The cationic component contains at least one partially water-soluble calcium salt and preferably at least one non-toxic, water-soluble salt of a divalent metal other than calcium. The anionic component contains at least one water-soluble phosphate salt, and at least one water-soluble fluoride salt. The separating means may be in the form of a liquid medium in which the anionic and cationic components are insoluble or in the form of a physical barrier. As used herein, the term "partially water-soluble" with respect to the calcium salt component means that the solubility of the salt is greater than that of dicalcium phosphate dihydrate in an aqueous solution having a pH of about 7.0 and a temperature of about 25° C. but wherein less than 0.25 gram of the calcium salt will dissolve in 100 ml of water at a temperature of 20° C. In an aqueous solution having a pH of about 7.0 at a temperature of about 25° C., dicalcium phosphate dihydrate generally releases about 40 ppm of calcium cations. Thus, the calcium salt used in the present invention generally has a minimum solubility such that the salt is capable of releasing more than about 40 ppm of calcium cations in an aqueous solution having a pH of about 7.0 at a temperature of about 25° C. Preferably, the calcium salt(s) used in this invention has a solubility in such aqueous solution such that the salt(s) releases from about 100 ppm to no more than about 1400 ppm of calcium cations.

The term "water-soluble" as used herein with respect to the phosphate, fluoride and divalent metal salts suitable for use in the present invention means that at least 0.25 gram of the salt will dissolve in 100 ml of water at a temperature of about 20° C.

In preferred embodiments, the products of this invention contain water, a concentration of dissolved calcium cations released by the calcium salt released in the water, and a concentration of an undissolved form of such calcium salt. Preferably, the cationic and anionic components of the products of this invention are both aqueous, wherein the cationic component contains no more than about 0.14%, more preferably no more than about 0.08%, most preferably from about 0.01% to about 0.05%, by weight of dissolved calcium cations released by the calcium salt, and at least about 0.05%, more preferably at least about 0.20%, most preferably from about 0.20% to about 0.30%, by weight of the undissolved form of the calcium salt.

The products of this invention may be in the form of one-part products or in the form of two-part products. Preferably, the products of this invention are in the form of two-part products.

One-part products of this invention contain the cationic and anionic components suspended in a non-aqueous, hydrophilic liquid carrier medium which acts as the separating means. Upon mixing of the one-part product with water and/or saliva, the liquid carrier medium releases the cationic and anionic components into the water and/or saliva so as to form the mixed aqueous composition. In preferred embodiments, the liquid carrier medium simultaneously releases the anionic and cationic components into the water and/or saliva.

The two-part products of this invention contain first and second discrete parts, wherein the first discrete part contains the cationic component and the second discrete part contains the anionic component. The separating means separates the first and second discrete parts from one another. In the two-part products of this invention, the anionic and cationic components are both in liquid form. The anionic and cationic components may both be aqueous or non-aqueous, or one component may be aqueous while the other component is non-aqueous. As stated previously herein, in preferred embodiments of the products of this invention, both the anionic and the cationic components are aqueous.

If the cationic and anionic components are both aqueous in the two-part products, the separating means is a physical barrier separating the first and second discrete parts from one another. If one or both of the cationic and anionic components are non-aqueous, the separating means can be a solid physical barrier or a non-solid barrier formed by the mutual insolubility of the cationic and anionic components. The two-part products of this invention further contain a dispensing means for dispensing the anionic and cationic components from the products. In preferred embodiments, the dispensing means is capable of simultaneously dispensing the anionic and cationic components from the product.

When a product within the scope of this invention is ready to be used, the cationic and anionic components are mixed together with water and/or saliva to form the mixed aqueous composition previously mentioned herein. The anionic and cationic components are mixed only when the components are introduced into the oral cavity or immediately before their introduction into the oral cavity.

The cationic and anionic components of the products of this invention must each have a pH in water such that the mixed aqueous composition has a pH of from about 4.0 to about 10.0, preferably from greater than about 4.0 to about 7.0, more preferably from about 4.5 to about 6.5, and most preferably from about 5.00 to about 5.75.

The partially water-soluble calcium salt(s) is present in the products of this invention in an amount such that in the mixed aqueous composition a first portion of the calcium salt(s) is present as dissolved calcium cations and a second portion of the calcium salt(s) is present as undissolved calcium salt. Preferably, the mixed aqueous composition will contain from about 100 ppm to no more than about 1400 ppm, more preferably from about 100 ppm to no more than about 800 ppm, most preferably from about 100 ppm to about 500 ppm, of the dissolved calcium cations. In addition, the mixed aqueous composition will preferably contain at least about 500 ppm, more preferably at least about 2000 ppm, most preferably from about 2000 ppm to about 3000 ppm, of the undissolved calcium salt.

If the product is a two-part product and the cationic component therein is aqueous, such aqueous cationic component will also contain dissolved calcium cations and undissolved calcium salt. The amount of dissolved calcium cations in the aqueous cationic component is preferably no more than about 0.14%, more preferably no more than about 0.08%, most preferably from about 0.01% about 0.05%, by weight of the cationic component. In addition, the amount of undissolved calcium salt in the aqueous cationic component is preferably at least about 0.05%, more preferably at least about 0.20% and most preferably from about 0.20% to about 0.30%, by weight of the cationic component.

The phosphate and fluoride salts are respectively present in the products of this invention in amounts such that the mixed aqueous composition will further contain dissolved phosphate anions and dissolved fluoride anions. In two-part products of this invention wherein the anionic component is aqueous, such aqueous anionic component will also contain dissolved phosphate anions and dissolved fluoride anions.

The mixed aqueous composition will preferably contain at least about 100 ppm, more preferably from about 500 ppm to about 40,000 ppm, of the phosphate anions; and preferably from about 100 ppm to about 5000 ppm, more preferably from about 850 ppm to about 2000 ppm, of the fluoride anions.

As stated hereinabove, the products of this invention further contain at least one non-toxic, water-soluble salt of a divalent metal other than calcium. If used, the divalent metal salt(s) releases divalent metal cations which help to stabilize the mixed aqueous composition against rapid precipitation of the calcium cations and the phosphate and fluoride anions. The remineralizing cations and anions can then diffuse through the tooth surface to the demineralized subsurface lesion(s) and/or the exposed dentin tubule with a reduced risk of forming a precipitate bound to the tooth surface. As a result, when an effective amount of the divalent metal cations is used, the subsurface lesion is more effectively remineralized or desensitized and/or the exposed dentin tubule is more effectively mineralized.

When used, the divalent metal salt(s) is preferably present in the products of this invention in an amount such that the mixed aqueous composition will contain at least about about 100 ppm, more preferably from about 500 ppm to about 40,000 ppm, of the divalent metal cations released by the divalent metal salt(s).

The products of this invention preferably contain from about 0.05% to about 15.0% by weight, more preferably from about 0.10% to about 10.0% by weight, of the calcium salt(s); from about 0.05% to about 15.0% by weight, more preferably from about 0.10% to about 10.0% by weight, of the phosphate salt(s); and from about 0.01% to about 5.0%, more preferably from about 0.02% to about 2.0%, by weight of the fluoride salt(s). In preferred embodiments, the products of this invention further contain at least 0.001%, preferably from about 0.0001% to about 2.0%, and more preferably from about 0.01% to about 1.0%, by weight of the divalent metal salt(s) discussed previously herein.

The products of this invention contain a molar ratio of the calcium salt(s) to the phosphate salt(s) of preferably from about 0.01:1 to about 100:1. Most preferably, the concentration of the calcium salt(s) and the concentration of the phosphate salt(s) are preferably essentially the same in the products of this invention. The concentration of the calcium salt(s) always exceeds the solubility of such salt, whereas the concentration of the phosphate salt(s) may be as high or even higher than the solubility thereof.

Non-limiting examples of calcium salts of partial water-solubility suitable for use in this invention include calcium sulfate, anhydrous calcium sulfate, calcium sulfate hemihydrate, calcium sulfate dihydrate, calcium dl-malate trihydrate, calcium tartrate, calcium malonate, calcium succinate, and mixtures of the foregoing. Calcium sulfate is preferred.

The partially water-soluble calcium salt component of the products of this invention can be prepared in situ, for example, by preparing mixtures of an acid such as, e.g., tartaric acid, and a water-soluble calcium salt such as, e.g., calcium nitrate, and adjusting the pH as needed.

In the present invention, the principle known as the "common ion effect" can be used to control the solubility of the partially water-soluble calcium salt used in the present invention and to optimize calcium release and fluoride stability. To achieve the common ion effect, a salt can be added to the product or solution of this invention wherein the anion of the salt is the same as the anion present in the calcium salt used in the particular product or solution. In the present invention, the sodium, potassium and ammonium salts are preferred for use to achieve the common ion effect. However, an anion which is part of another functional ingredient may also be added. For example, the use of magnesium sulfate in a calcium sulfate-based formulation would supply at least some of the needed sulfate anion.

Suitable water-soluble inorganic phosphate salts for use in the present invention include, for example, alkali salts and ammonium salts of orthophosphoric acid, such as, e.g., potassium, sodium or ammonium orthophosphate; monopotassium phosphate; dipotassium phosphate; tripotassium phosphate; monosodium phosphate; disodium phosphate and trisodium phosphate.

Suitable fluoride salts for use in the present invention include the alkali fluorides such as sodium, potassium, lithium or ammonium fluoride; tin fluoride; indium fluoride; zirconium fluoride; copper fluoride; nickel fluoride; palladium fluoride; fluorozirconates such as sodium, potassium or ammonium fluorozirconate or tin fluorozirconate; fluorosilicates; fluoroborates; and fluorostannites.

Organic fluorides, such as the known amine fluorides, are also suitable for use in the products of the present invention.

Water-soluble alkali metal monofluoro-phosphates such as sodium monofluorophosphate, lithium monofluorophosphate and potassium monofluorophosphate, (the sodium monofluorophosphate being preferred) may be employed. In addition, other water-soluble monofluorophosphate salts may be employed, including, for example, ammonium monofluorophosphate, aluminum monofluorophosphate, and the like. If monofluorophosphate salts are used as the fluoride source in two-phase systems, these salts could be present in the first phase along with the calcium cations without departing from the present invention. However, this is less desirable due to the potential loss of fluoride as a result of the formation of sparingly soluble calcium fluoride.

The divalent metal salt(s) which can be used in the products of the present invention may be any water-soluble, non-toxic divalent metal compound which will stabilize the calcium, phosphate and fluoride ions so that these ions do not rapidly or prematurely precipitate before diffusing into the teeth. In practice, however, it has been found that at least one member selected from the group consisting of magnesium, strontium, tin, and zinc, with magnesium being preferred, is the most effective divalent metal in stabilizing the system.

Suitable magnesium compounds include, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds include, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds include, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds include, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

As stated previously herein, the separating means used in the one-part products of this invention is preferably a non-aqueous, hydrophilic liquid carrier medium, the term "liquid" being defined as set forth previously herein. Such non-aqueous liquid carrier mediums include any carrier medium which is conventionally used in such dental products as toothpastes, gels, creams, mouthwashes and rinses. Examples of suitable non-aqueous carrier mediums include non-aqueous solvents such as, e.g., ethyl alcohol, glycerine and propylene glycol. Preferably, the non-aqueous, hydrophilic liquid carrier medium is a polyethylene oxide having a molecular weight of about 400 (also known under the designation "Carbowax 400").

As stated previously herein, in the two-part products of this invention, the anionic and cationic components may both be aqueous or non-aqueous, or one component may be aqueous and the other component non-aqueous.

In the two-part products of this invention, if one or both of the cationic and anionic components are aqueous, the mixed aqueous composition can be formed by dispensing the cationic and anionic components from the product and simply mixing the two components together. If neither component is aqueous, the mixed aqueous composition can be formed by mixing the two dispensed components with saliva and/or water in the mouth or with water provided from an external source.

While completely aqueous compositions are preferred in the present invention for application to the teeth, non-aqueous solvents may be employed in combination with water and/or saliva to form an aqueous/non-aqueous medium. Suitable non-aqueous solvents include, e.g., ethyl alcohol, glycerine and propylene glycol. Solvent systems suitable for use in the present invention are those which are safe for use in the mouth.

As stated previously herein, the mixed aqueous composition formed by mixing the cationic and anionic components with water and/or saliva has a pH of from about 4.0 to about 10.0, preferably from greater than about 4.0 to about 7.0, more preferably from about 4.5 to about 6.5, and most preferably from about 5.0 to about 5.75. At a pH within such range, enough of the calcium cations, phosphate anions and fluoride anions remain soluble for the period of time required to remineralize the subsurface lesions and/or mineralize the exposed tubules of the dental enamel. If the mixed aqueous composition has a pH below about 3, demineralization will occur rapidly. A pH below about 2.5 is undesirable from a safety standpoint.

The pH of the mixed aqueous composition may be adjusted to the desired pH by methods well known in the art. The pH may be lowered by the addition of any acid which is safe for use in the oral cavity and which yields the desired pH at the amount employed. Examples of suitable acids include acetic acid, phosphoric acid, citric acid and malic acid.

The mixed aqueous composition and the insoluble precipitate formed therefrom in the present invention must both have acceptable levels of toxicity (i.e., the particular ions, in the amounts used in the remineralization/mineralization process, must be non-toxic) and must both be otherwise compatible in the oral environment.

The present invention further provides methods of remineralizing one or more lesions formed in a subsurface of at least one tooth and/or one or more exposed tubules in a dentin portion of at least one tooth. Broadly, the methods of this invention involve the steps of:

(1) providing the previously-described mixed aqueous composition; and (2) applying the mixed aqueous composition to the tooth for a period of time sufficient to allow diffusion of the calcium cations, the phosphate anions and the fluoride anions through a surface of the tooth to the subsurface and/or to the dentin portion, wherein the cations and anions precipitate at the subsurface to form an insoluble salt on the lesion(s) so as to remineralize the lesion(s), and/or precipitate at the dentin portion to form an insoluble salt on the exposed tubule(s) so as to mineralize the exposed tubule(s).

The mixed aqueous composition is applied to the tooth for preferably at least about 10 seconds, more preferably at least about 30 seconds, and most preferably at least about 1 minute. The delayed precipitation of the anions and cations for a time period sufficient to permit the ions to diffuse to the dentin and/or subsurface lesion is a benefit accruing at least in part from the use in this invention of the partially water-soluble calcium salt(s). The presence of the divalent metal salt(s) further promotes such delayed precipitation.

The pH of the mixed aqueous composition remains relatively constant after its introduction into or initial formation in the oral cavity. Under some conditions, calcium fluoride phosphate readily precipitates at this pH, but most surprisingly, while some precipitation may occur immediately and to a small extent even before application to the teeth, substantially greater amounts of calcium, phosphate and fluoride ions remain in solution to diffuse into the teeth and remineralize the demineralized dental enamel. As stated hereinabove, this delayed precipitation is due at least in part to the use of the partially water-soluble calcium salt(s) in the present invention, with the divalent metal salt(s) also playing an important role.

In general, the partially water-soluble calcium salt(s) is such that the amount of dissolved calcium cations in the mixed aqueous composition is such that the concentration of dissolved fluoride anions in the mixed aqueous composition is equal to at least 75% by weight of fluoride anions in the fluoride salt in the product for a period of up to about 1 minute after formation of the mixed aqueous composition.

When the aqueous anionic component is aqueous and contains the fluoride salt(s) as dissolved fluoride anions, it has been found that the mixed aqueous composition of the present invention has a concentration of fluoride anions equal to about at least about 75% of the concentration of fluoride anions in the aqueous anionic component for a period of up to about 1 minute after formation of the mixed aqueous composition. In other words, at least about 75% by weight of the fluoride anions in the anionic aqueous component remains available for absorption in the mixed aqueous composition. This is an important benefit provided by the products and methods of this invention.

Therefore, the use of partially water-soluble calcium salt(s) in the products of this present invention allows a higher level of free fluoride anions to be present in the mixed aqueous composition and thus available for absorption.

As stated previously herein, the use of the partially water-soluble calcium salt(s) in this invention also provides a benefit in that as the calcium cations in the mixed aqueous composition are precipitated, the undissolved calcium salt releases additional calcium cations to the composition so as to maintain the rate of the remineralization and/or mineralization process.

When using the two-part aqueous products of this invention, the time period between the mixing of the first and second parts and the application of the resulting mixed aqueous composition to the teeth should not exceed 1 minute, and preferably is less than 1 minute. With a toothpaste, gel, and the like, mixing is achieved on the surface to the teeth while brushing. An important feature of the present invention lies in the mixing of the anionic and cationic components and the quick and timely application of the resulting mixed composition to the tooth so that the ions will diffuse through the surface of the tooth to the dentin and/or subsurface of the tooth, where the ions will precipitate calcium phosphate, calcium fluoride, and calcium fluoroapatite in the dentin and/or subsurface enamel of the teeth. However, before such precipitation occurs, the mixed aqueous composition must quickly be applied to the teeth.

The remineralizing-mineralizing precipitate formed in the present invention is a calcium phosphate or a hydroxyapatite (the natural constituent of tooth enamel) with incorporated fluoride ions. Because of the presence of the fluoride ions in the mixed aqueous composition used in this invention, the remineralized enamel is more resistant to demineralization than was the original enamel. Therefore, use of the mixed aqueous composition in accordance with the present invention not only remineralizes the enamel but also renders such enamel more resistant to subsequent demineralization than was the original enamel.

In preferred embodiments, the products of this invention are in the form of toothpastes, gels, professional gels, creams, mouthwashes or mouthrinses. More preferably, the products of this invention are in the form of two-part aqueous products, wherein the anionic and cationic components are both aqueous.

A two-part aqueous product within the scope of this invention can be prepared as follows. At least one calcium salt of partial water-solubility in a concentration of from about 0.05% to about 15.0% by weight is mixed in an aqueous medium to form a cationic aqueous composition containing calcium cations and undissolved calcium salt. At least one water-soluble divalent metal salt other than a calcium salt can be added to the cationic aqueous composition at a concentration of greater than about 0.001% by weight and preferably from about 0.001% to about 2.0% by weight. At least one water-soluble phosphate salt at a concentration of from about 0.05% to about 15.0% by weight is dissolved in an aqueous medium to form an anionic aqueous composition. At least one water-soluble fluoride salt is added to the anionic aqueous composition at a concentration of from about 0.01% to about 5.0% by weight. The pH of each composition is adjusted so that, upon mixing, the pH of the final mixed aqueous composition will range from about 4.0 to about 10.0. The two aqueous compositions are then mixed to produce a stable supersaturated or nearly supersaturated aqueous composition of calcium fluoride phosphate containing excess undissolved calcium salt.

In addition to the active anionic and cationic salts previously described herein, toothpaste, gel and cream products within the scope of this invention preferably further contain from about 0.5% to about 65%, preferably from about 5% to about 40%, by weight of an abrasive; from about 0.2% to about 5% by weight of a sudsing agent; from about 0.1% to about 5% by weight of a binding agent; from 0% to about 50% by weight of a humectant; and the balance, water and minors. From about 1.0% to about 10.0% by weight of an inorganic thickener such as hydrated silica may also be added.

Suitable abrasives which can be used in the present invention include, for example, silica xerogels. Other conventional toothpaste abrasives can be used in the products of this invention, such as, e.g., beta-phase calcium pyrophosphate, dicalcium phosphate dihydrate, anhydrous calcium phosphate, calcium carbonate, zirconium silicate, and thermosetting polymerized resins. Silica aerogels and insoluble metaphosphates such as insoluble sodium metaphosphate can also be used. Mixtures of abrasives can be also be used. Silica xerogel abrasives are preferred.

Suitable sudsing agents for use in the present invention include those which are reasonably stable and which form suds throughout the period of application. Preferably, nonsoap anionic or nonionic organic synthetic detergents are employed. Examples of such agents include, e.g., water-soluble salts of alkyl sulfate having from 10 to 18 carbon atoms in the alkyl radical, such as sodium lauryl sulfate; water-soluble salts of sulfonated monoglycerides of fatty acids having from 10 to 18 carbon atoms, such as sodium monoglyceride sulfonate; salts of $C_{10}$–$C_{18}$ fatty acid amides of taurine, such as sodium N-methyl taurate; salts of $C_{10}$–$C_{18}$ fatty acid esters of isothionic acid; and substantially saturated aliphatic acyl amides of saturated monoaminocarboxylic acids having 2 to 6 carbon atoms, and in which the acyl radical contains 12 to 16 carbon atoms, such as sodium-N-lauryl sarcoside. Mixtures of two or more sudsing agents can be used.

A binding material can be added to thicken and provide a desirable consistency to the products of the present invention. Suitable thickening agents include, e.g., water-soluble salts of cellulose ethers, such as, for example, sodium carboxymethyl cellulose, hydroxypropyl cellulose, and hydroxyethyl cellulose. Natural gums such as gum karaya, gum arabic, carrageenan and gum tragacanth, can also be used. Colloidal magnesium aluminum silicate, silica aerogels, silica xerogels, fumed silica, or other finely divided silica can be used as part of the thickening agent for further improved texture. A preferred thickening agent is xanthan gum.

It is also desirable to include some humectant material in toothpaste or gel embodiments of the present invention to keep such products from hardening. Suitable humectants include, e.g., glycerine, sorbitol, polyethylene glycol, propylene glycol, and other edible polyhydric alcohols, as well as mixtures thereof.

Toothpaste or gel products within the scope of this invention may also contain flavoring agents such as, for example, oil of wintergreen, oil of peppermint, oil of spearmint, oil of sassafras, and oil of clove.

Toothpaste or gel products of the present invention may also contain sweetening agents such as, e.g., saccharin, dextrose, levulose, sodium cyclamate, and aspartame. Mixtures of sugar with a sweetener, e.g., sucralose, are also contemplated for use in the present invention.

It is also possible to manufacture the dentifrice products of the present invention in the form of a transparent or translucent gel. This is accomplished by matching the refractive index of the water-humectant system with the abrasives and inorganic thickeners if used.

Professional gels can be formulated similar to dentifrices but with higher fluoride contents. Since these products are not designed for cleaning but only as a fluoride application, abrasives and other cleaning agents need not be included in the formulation.

Other products within the scope of this invention include mouthwashes and rinses. Mouthwashes and rinses generally contain an aqueous solution of ethyl alcohol and flavoring materials. The alcohol provides an antibacterial effect, solubilizes the flavoring materials and provides a pleasant mouth feeling. Alcohol-free mouthwashes are now, however, gaining in popularity. Optionally, mouthwashes and rinses also contain additional antibacterial agents and humectants such as glycerine and sorbitol which give a moist feeling to the mouth.

In addition to the anionic and cationic active ingredients discussed previously herein, mouthwashes and rinses preferably contain from about 0 to about 30%, preferably from about 0 to about 20%, by weight of ethyl alcohol; from about 30% to about 90% by weight of water; from about 0 to about 20% by weight of glycerine or other humectant; from about 0 to about 0.1% by weight of an antibacterial agent; from about 0 to about 0.2% by weight of a soluble fluoride source; from about 0.01% to about 0.5% by weight of a sweetening agent; from about 0.01% to about 2.0% by weight of a flavoring agent; and from about 0.1% to about 1% by weight of an emulsifier-surfactant.

The present invention further provides a two-part packaged product composed of:

(i) a first discrete part containing the aforementioned cationic component in liquid form;

(ii) a second discrete part containing the aforementioned anionic component in liquid form;

(iii) a dispensing container containing a first discrete compartment and a second discrete compartment each with an outlet end, wherein the first compartment stores the first discrete part and the second compartment stores the second discrete part;

(iv) a closure mechanism for closing the first compartment and the second compartment; and (v) a dispensing means for simultaneously dispensing the liquid cationic component and the liquid anionic component from the product.

A plurality of packaging methods may be employed in order to separately contain or store the two components and provide effective dispensing thereof into the oral cavity.

Thus, the two components of a toothpaste, gel, cream, or the like, may be simultaneously dispensed from separate collapsible tubes preferably made of plastic, a plastic and metal laminate, etc. For convenience and in order to aid in dispensing substantially equal amounts of the components, the tubes may be held together by banding or cementing, preferably along the corresponding ventral sides of the tubes.

In another embodiment, the two tubes may be constructed to have abutting, preferably flat, sidewall portions. In the foregoing embodiments, the mouths of the tubes are usually sufficiently close so that sufficient quantities of the components of the toothpaste or gel may be simultaneously dispensed directly on the toothbrush with the tubes being capped separately.

Alternatively, another packaging method involves loading each component of the paste or gel into separate compartments of the same collapsible composite tube, joined by a common orifice. Such composite tube has compartments separated by a divider which is firmly attached along substantially diametrically opposed portions of the sidewall, and corresponding portions of the head structure of the tube. The divider may be glued or welded to the sidewall and head structure of the tube during manufacture of the latter. The divider is preferably provided with a protruding portion which extends into the mouth of the tube until its edge is substantially flush with the rim of the mouth. Thus, a divider forms with the sidewall two separate compartments of substantially the same volume for storage of the cationic and anionic components, respectively.

In another alternative packaging method, the two tubes are "concentric". An inner tube lies within and parallel with an outer tube. The mouths of the tubes abut at the same point. Protrusions or the like are inserted between the inner and outer tubes so that the component contained in the outer tube can pass through an available space between the mouth of the outer tube and the mouth of the inner tube. The closures of this tube-within-a-tube (which can screw on the outer tube or simply be held by pressure} may, but does not have to be, equipped with an interior protrusion to fit in the inner tube in order to prevent premature intermixing of the two components at the mouth of the tube.

The tubes of all the above embodiments are usually filled from the bottom and are subsequently sealed together by conventional techniques.

Another alternative packaging arrangement is a pressurized container which is provided with two compartments and two spouts. The internal pressure of the compartments is maintained by a pressurized gas, i.e., nitrogen, at the bottom of each compartment. Operation of a mechanical actuator actuates valves which release the contents of the compartments through the spouts, causing discharge of the paste or gel components onto a brush.

The mouthwash, rinse or similar liquid embodiments are maintained in a manner similar to the pastes or gels in that, during storage, each of the components are maintained separate from one another to prevent premature reaction. Upon dispensing, the components mix and react in the oral cavity to effect remineralization of dental enamel. The liquid components can therefore be stored each in separate compartments of a dual-compartment dispenser. The dispenser usually includes a closure system containing, for example, an inclined crown portion, at least two pouring spouts extending upwardly from an upper surface of the crown portion, and a cover for securement to the crown portion. The cover is provided with closure means, for example, depending plugs, to close the closure. Each pouring spout is preferably provided with a vent opening in addition to product orifices in the spouts. The orifices can be positioned close together on the crown, all of which assists in achieving control over pouring. Transparent containers have proven to be the most satisfactory. Transparency aids a person's ability to accurately and controllably dispense relatively equal volumes from a dual-compartment dispenser. Transparent walled containers also serve a window function for gauging the amounts of liquid remaining in the dispenser. The walls of the containers can be scribed or otherwise calibrated to assist in dispensing the correct remineralizing amount of the mixed aqueous composition.

The following Examples illustrate the invention. In the Examples and elsewhere herein, parts and percentages are by weight unless otherwise stated.

Experimental

The examples below show that the products of this invention increase the hardness of teeth and promote fluoride uptake more effectively than do conventional toothpastes containing fluoride alone.

The following test method was used in the examples below. Human enamel chips taken from whole teeth were each mounted in a plastic rod with a single surface of each chip exposed. Artificial lesions, from about 50 to about 100 microns deep, were formed in the exposed surfaces of the chips by treating the surfaces with a demineralizing Carbopol gel for approximately 72 hours. After such treatment was completed, the surface hardness of the chips was measured.

The chips (eight per test) were then treated with test products as part of an in vitro multicyclic regimen which simulated conditions in the mouth. The regimen cycle consisted of a 30-minute demineralization in a standard demineralizing solution, followed by a 5-minute treatment with the test products, either diluted or undiluted, followed by a 60-minute remineralization in whole human saliva. Overnight, which was every fifth cycle, the specimens were kept with a layer of saliva on the surface thereof and stored in a cold room. The complete test ran for three days for a total of fifteen cycles.

EXAMPLES 1–7 and Control Examples A and B

In Examples 1–7 and Control Examples A and B, the remineralizing properties of two-part toothpaste products within the scope of this invention (Examples 1–7) are compared with those of one-part toothpaste products outside the scope of the invention (Control Examples A and B).

In Example 1 and Control Example A, the products were used undiluted to simulate what happens when the teeth are brushed without dilution with saliva. In Example 1, the two parts of the test dentifrice (which was a partial formulation because it did not contain flavor and had a reduced level of thickener) were placed together to form a mixture. The enamel chips were immediately immersed in the mixture and stirring was initiated. Control Example A used a product similar in composition to commercial sodium fluoride-containing toothpastes but somewhat thinner to aid mixing during treatment. In Control Example A, the chips were immersed in the one-part product and mixing was initiated.

In Examples 2–7 and Control Example B, the products were used diluted in human saliva to simulate conditions during brushing after the products have been diluted by saliva present in the mouth. Thus, in the treatment cycle, the two parts of the toothpastes used in Examples 2–5 were separately diluted at 1 part formulation to 2 parts saliva and mixed together immediately before immersion of the enamel specimens. This prevents premature reaction of the toothpaste ingredients. The product used in Control Example B was Crest® toothpaste, which contains sodium fluoride. The Control B product was also diluted at 1 part formulation to 2 parts saliva, and the enamel specimen was immersed in the resulting solution.

The formulations of the products used in Examples 1–7 are presented in Table 1. The weight percentages recited in Table 1 are based on the combined weight of the two parts. The formulation of the product used in Control Example A is presented in Table 2, the weight percentages recited therein being based on the total weight of the one-part product. As stated above, the product used in Control Example B was Crest® toothpaste, which contains sodium fluoride.

In the tables below, the following terms have the following meanings:

"Carbowax"—a tradename for polyethylene glycol; also known as "PEG 8". The Carbowax product used in the examples herein has an average molecular weight of 400.

"Tween 20"—a tradename for polyoxyethylene-20-sorbitan monolaurate.

"Zeodent 113"—an abrasive containing hydrated silica.

"Zeodent 165"—an inorganic thickener containing hydrated silica.

"TISAB"—a buffer solution which regulates pH, provides ionic strength adjustment and eliminates interferences due to the presence of trace metals. TISAB solution contains sodium acetate, sodium chloride, acetic acid, and 1,2-cyclohexane diaminetetraacetic acid.

TABLE 1

Examples 1–7: Formulations

| Ingredients | 1 | 2 | 3 | 4 | 5 | 6 | 7 |
|---|---|---|---|---|---|---|---|
| Part (A) | | | | | | | |
| Calcium Sulfate | 0.85 | 0.85 | 0.85 | 0.85 | 0.85 | 1.04 | 0.85 |
| Magnesium Chloride | 0.40 | 0.40 | 0.40 | 0.40 | 0.40 | 0.49 | 0.40 |
| Water | 5.00 | 4.99 | 19.99 | 19.99 | 19.99 | 24.37 | 45.20 |
| Malic Acid | 0.85 | 0 | 0 | 0 | 0 | 1.04 | 0.85 |
| Ammonium Chloride | 1.75 | 0 | 0 | 0 | 0 | 2.14 | 2.25 |
| NaOH | 0.40 | 0 | 0 | 0 | 0 | 0.49 | 0.45 |
| Glycerin | 19.40 | 21.80 | 6.60 | 19.10 | 6.60 | 6.10 | 0 |
| Sorbitol | 12.49 | 12.50 | 12.50 | 0 | 12.50 | 13.23 | 0 |
| PEG 8 | 0 | 1.00 | 1.00 | 1.00 | 1.00 | 0 | 0 |
| Methyl Paraben | 0.03 | 0.03 | 0.03 | 0.03 | 0.03 | 0 | 0 |
| Propyl Paraben | 0.03 | 0.03 | 0.03 | 0.03 | 0.03 | 0 | 0 |
| CMC | 0.50 | 0.15 | 0.35 | 0.35 | 0.35 | 0.61 | 0 |
| Saccharin | 0.30 | 0.25 | 0.25 | 0.25 | 0.25 | 0.37 | 0 |
| Zeodent 113 | 7.00 | 7.00 | 7.00 | 7.00 | 7.00 | 0 | 0 |
| Zeodent 165 | 1.00 | 1.00 | 1.00 | 1.00 | 1.00 | 0 | 0 |
| Part (B) | | | | | | | |
| Water | 21.01 | 20.00 | 20.00 | 20.00 | 19.50 | 25.13 | 48.46 |
| Sodium Fluoride | 0.24 | 0.25 | 0.25 | 0.25 | 0.25 | 0.29 | 0.24 |
| Monoammonium Phosphate | 1.10 | 0 | 0 | 0 | 0 | 1.33 | 0 |
| Monopotassiuin Phosphate | 0 | 0 | 0 | 2.45 | 1.20 | 0 | 1.30 |
| Diammonium Phosphate | 0 | 2.80 | 2.80 | 0 | 1.40 | 0 | 0 |
| Glycerin | 5.00 | 5.00 | 5.00 | 17.15 | 5.00 | 6.03 | 0 |
| Sorbitol | 12.50 | 10.55 | 10.55 | 0 | 12.50 | 15.06 | 0 |
| PEG 8 | 1.00 | 1.00 | 1.00 | 1.00 | 1.00 | 1.20 | 0 |
| Sodium Saccharin | 0.30 | 0.30 | 0.30 | 0.30 | 0.30 | 0.36 | 0 |
| CMC | 0.35 | 0.35 | 0.35 | 0.35 | 0.35 | 0.60 | 0 |
| Zeodent 113 | 7.00 | 7.00 | 7.00 | 7.00 | 7.00 | 0 | 0 |
| Zeodent 165 | 1.00 | 1.00 | 1.00 | 1.00 | 1.00 | 0 | 0 |
| Malic Acid | 0 | 1.25 | 1.25 | 0 | 0 | 0 | 0 |

TABLE 1-continued

Examples 1–7: Formulations

Example No. Concentration (parts by weight)

| Ingredients | 1 | 2 | 3 | 4 | 5 | 6 | 7 |
|---|---|---|---|---|---|---|---|
| Sodium Lauryl Sulfate | 0.50 | 0.50 | 0.50 | 0.50 | 0.50 | 0 | 0 |
| TOTAL | 100.00 | 100.00 | 100.00 | 100.00 | 100.00 | 100.00 | 100.00 |

TABLE 2

Control Example A: Formulation

| Ingredients | Concentration (parts by weight) |
|---|---|
| Water | 20.58 |
| Sodium Fluoride | 0.24 |
| Monoammonium Phosphate | 0.20 |
| Monopotassium Phosphate | 0.82 |
| Glycerin | 17.56 |
| Sorbitol | 43.28 |
| Sodium Saccharin | 0.22 |
| CMC | 0.60 |
| Sodium Lauryl Sulfate | 1.50 |
| Flavor | 1.00 |

The respective concentrations of dissolved calcium cations and undissolved calcium salt in part (A) of the formulations of Examples 1–7 are set forth in Table 3 below. The weight percentages given in Table 3 are based on the combined weight of the two parts of the products.

TABLE 3

Examples 1–7
Part (A): Dissolved and Undissolved Calcium Content

| | Concentration (Based on the weight of Part (A)) | |
|---|---|---|
| Example No. | Dissolved Calcium Cations | Undissolved Calcium Salt |
| 1 | 0.01% | 0.01% |
| 2 | 0.01% | 0.24% |
| 3 | 0.035% | 0.215% |
| 4 | 0.015% | 0.235% |
| 5 | 0.035% | 0.215% |
| 6 | 0.04% | 0.26% |
| 7 | 0.04% | 0.21% |

The average increase in hardness and the average fluoride uptake of the products used in Examples 1–7 and Control Examples A and B were measured. The results are presented in Table 4 below.

TABLE 4

Examples 1–7 and Control Examples A and B:
Average Hardness Increase and Fluoride Uptake

| Example No. | Average Hardness Increase | Average Fluoride Uptake |
|---|---|---|
| 1 | 42% | 8307 ppm |
| A | 18% | 4020 ppm |
| 2 | 10.7% | 6213 ppm |
| 3 | 9.83% | 6248 ppm |
| 4 | 11.9% | 6127 ppm |
| 5 | 10.75% | 5794 ppm |
| 6 | 17.97% | 4470 ppm |
| 7 | 17.78% | 5219 ppm |
| B | 2.72% | 3971 ppm |

The results presented in Table 4 show that the products of the present invention are much more effective in remineralizing lesions than are the Control products. The results set forth in Table 4 also show that, in Examples 1–7, when the two parts of the product were mixed during brushing, the amount of calcium cations relesase by the partially water-soluble calcium sulfate was sufficient to promote remineralization but insufficient to precipitate the fluoride. Thus, the maximum level of fluoride anions remained available for absorption by the tooth during use of the products.

EXAMPLES 8 and Control Examples C and D

Example 8 and Control Examples C and D illustrate the advantage of using a partially water-soluble calcium salt over other calcium salts.

As stated previously herein, in the products of this invention, the concentration of dissolved calcium cations in the calcium-containing (i.e. cationic) portion of the toothpaste is limited by using a partially water-soluble calcium salt. Under these conditions, the loss of free fluoride by the formation of insoluble calcium fluoride is minimized when the two parts of the formulation are mixed. However, an effective level of calcium cations is maintained when the toothpaste is diluted because of further dissolution of the undissolved calcium salt. Example 8 and Control Examples C and D show how the free fluoride concentration is maintained in solution when the two parts of the product are mixed in water to a concentration which is typically found in the mouth after dilution with saliva, i.e., about 1 part complete toothpaste to 3 parts saliva.

The formulations of the products used in Examples 8 and Control Examples C and D are shown in Table 5 below. The weight percentages recited for the ingredients in Example 8 and Control Examples C and D are based on the combined weight of the two parts.

TABLE 5

Example 8 and Control Examples D and E: Formulations

| | Concentration (weight percent) Example No. | | |
|---|---|---|---|
| Ingredient | 8 | D | E |
| Part A | | | |
| Calcium sulfate | 0.85 | 0 | 0 |
| Calcium nitrate | 0 | 1.50 | 0 |
| Calcium lactate | 0 | 0 | 1.95 |
| Glycerin | 22.14 | 21.49 | 21.04 |
| Sorbitol | 12.50 | 12.50 | 12.50 |
| Carbowax | 1.00 | 1.00 | 1.00 |
| CMC | 0.15 | 0.15 | 0.15 |
| Water | 5.00 | 5.00 | 5.00 |
| Methyl paraben | 0.03 | 0.03 | 0.03 |
| Propyl paraben | 0.03 | 0.03 | 0.03 |
| Saccharin | 0.30 | 0.30 | 0.30 |
| Zeodent 113 | 7.00 | 7.00 | 7.00 |
| Zeodent 165 | 1.00 | 1.00 | 1.00 |
| Part B | | | |
| Glycerin | 5.00 | 5.00 | 5.00 |
| Sorbitol | 9.81 | 9.81 | 9.81 |
| Carbowax | 1.00 | 1.00 | 1.00 |
| CMC | 0.35 | 0.35 | 0.35 |
| Water | 20.50 | 20.50 | 20.50 |
| Sodium fluoride | 0.24 | 0.24 | 0.24 |
| Monoammonium phosphate | 2.80 | 2.80 | 2.80 |
| Malic acid | 1.50 | 1.50 | 1.50 |
| Sodium lauryl sulfate | 0.50 | 0.50 | 0.50 |
| Saccharin | 0.30 | 0.30 | 0.30 |
| Zeodent 113 | 7.00 | 7.00 | 7.00 |
| Zeodent 165 | 1.00 | 1.00 | 1.00 |
| Total | 100.00 | 100.00 | 100.00 |

In Example 8, it was estimated that part A contained about 1000 parts per million (ppm) of dissolved calcium cations and about 2400 ppm undissolved calcium salt, the ppm-being based on the combined weight of the two parts. On diluting the two parts at 1 part toothpaste to 3 parts saliva, about 600 ppm of dissolved calcium cations (based on the combined weight of parts A and B) would be present and available for remineralization and/or mineralization.

In each of Example 8 and Control Examples C and D, five grams of part A were placed with five grams of part B in a beaker. With a high speed stirrer, the completed formulation (i.e., parts A and B together) was mixed with 30 milliliters of distilled water for exactly 60 seconds. The resulting composition was then filtered through an 0.45 micron filter and analyzed for soluble fluoride (i.e., free fluoride) by diluting 1 milliliter of the solution to 100 milliliters of water/TISAB (50:50) and comparing the fluoride electrode response with fluoride standards. The free fluoride levels, expressed as parts per million (ppm) based on the combined weight of parts A and B, are presented in Table 6 below.

TABLE 6

Example 8 and Control Examples C and D: Free Fluoride Content

| Example No. | Free Fluoride Content |
|---|---|
| 8 | 1040 ppm |
| C | 720 ppm |
| D | 440 ppm |

The results shown in Table 6 indicate that very little fluoride is lost when calcium sulfate (a partially water-soluble salt) is used. However, significant losses of fluoride were detected when the more soluble calcium lactate and calcium nitrate were used.

EXAMPLES 9 AND 10

When teeth are initially brushed with a toothpaste, very low quantities or even no saliva may be present in the mouth. A significant portion of the population suffers from low salivary flow. Thus, in some situations, mixing of the two parts of the formulation may occur without salivary dilution. Under these more stringent conditions, where fluoride and calcium are more likely to react, it is highly desirable for the free fluoride levels to remain high. In a preferred embodiment of the invention, a divalent metal salt such as magnesium, tin, zinc or strontium is added to the calcium portion of the dentifrice. This serves to prevent a premature loss of fluoride from the mixture when the two parts of the dentifrice are mixed together.

Examples 9 and 10 both fall within the scope of this invention. However, Example 9 contains magnesium chloride whereas Example 10 does not. The complete formulations of the products in Examples 9 and 10 are set forth in Table 7 below. The weight percentages recited in Table 7 are based on the combined weight of the two parts.

TABLE 7

Examples 9 and 10: Formulations

| | Concentration (weight percent) Example No. | |
|---|---|---|
| Ingredient | 9 | 10 |
| Part A | | |
| Calcium sulfate | 2.85 | 2.85 |
| Calcium nitrate | 0 | 0 |
| Magnesium chloride | 0.4 | 0 |
| Glycerine | 5 | 5 |
| Sorbitol | 10 | 10 |
| Carbowax | 1 | 1 |
| CMC | 0.5 | 0.5 |
| Water | 18.9 | 19.3 |
| Methyl Paraben | 0.03 | 0.03 |
| Propyl Paraben | 0.02 | 0.02 |
| Saccharin | 0.3 | 0.3 |
| Zeodent 113 | 7 | 7 |
| Zeodent 165 | 2.5 | 2.5 |
| Flavor | 0.5 | 0.5 |
| Tween | 0.5 | 0.5 |
| SLS | 0.5 | 0.5 |
| Part B | | |
| Glycerine | 5 | 5 |
| Sorbitol | 9.81 | 9.81 |
| Carbowax | 1 | 1 |
| CMC | 0.5 | 0.5 |
| Water | 19.69 | 19.69 |
| Sodium Fluoride | 0.25 | 0.25 |
| Monoammonium Phosphate | 2.45 | 2.45 |
| Sodium Saccharin | 0.3 | 0.3 |
| Zeodent 113 | 7 | 7 |
| Zeodent 165 | 2.5 | 2.5 |
| Flavor | 0.5 | 0.5 |
| Tween | 0.5 | 0.5 |
| SLS | 0.5 | 0.5 |
| Total | 100 | 100 |

In Examples 9 and 10, five grams of part A of each formulation was placed with five grams of part B in a beaker. The completed formulation was mixed without the addition of water for 30 seconds. Thirty milliliters of distilled water were then added and the mixture was stirred for exactly 60 seconds. The resulting composition was then filtered through an 0.45 micron filter and analyzed for soluble fluoride (i.e., free fluoride) by diluting 1 milliliter of the solution in 100 milliliters of water/TISAB (50:50) and comparing the fluoride electrode response with fluoride standards. Table 8 below sets forth the concentrations of free fluoride found, expressed as parts of free fluoride per million parts of the complete toothpaste formulation.

TABLE 8

Examples 9 and 10: Free Fluoride Content

| Example No. | Free Fluoride (ppm) |
|---|---|
| 9 | 1066 |
| 10 | 647 |

Examples 9 and 10 illustrate the benefit of adding a divalent metal cation, such as magnesium, to the calcium part of the toothpaste to prevent loss of fluoride anions upon mixing.

The level of dissolved calcium cations in the complete Example 9 toothpaste formulation before mixing was estimated by preparing part A of the composition without the Zeodent components (i.e., the hydrated silicas), CMC, flavor or surfactants; mixing overnight; and then filtering the resultant solution to remove undissolved calcium sulfate. The level of calcium cations was then measured by diluting 5 milliliters of the composition with 100 milliliters in water containing 2 milliliters of 4M potassium chloride ionic strength adjustor and comparing the calcium electrode response with standards. The concentration of dissolved calcium cations in Example 9 expressed as parts of calcium per million parts of the complete toothpaste formulation was thus estimated to be about 630 ppm. The quantity of undissolved calcium salt in this formulation was about 7800 ppm. A similar level of dissolved and undissolved calcium cations would be expected to be present in Example 10.

EXAMPLES 11–14 and

Control Examples E–J

Examples 11–14 and Control Examples E–J illustrate how the calcium concentration can be controlled using a partially soluble calcium salt. This is done either by direct addition of the partially soluble calcium salt or by combining a soluble calcium salt with an acid with which it forms a partially soluble salt such as malic acid or tartaric acid. The net result of this combination is the formation of the partially soluble calcium salt.

The complete formulations and pH values of the products prepared in Examples 11–14 are presented in Table 9. Table 10 sets forth the complete formulations, as well as the pH values, of the products prepared in Control Examples E–J. The weight percentages recited in Tables 9 and 10 are based on the combined weight of the two parts. The pH values were measured using a 10% solution in water.

TABLE 9

Examples 11–14: Formulations

| | Concentration (weight percent) Example No. | | | |
|---|---|---|---|---|
| Ingredient | 11 | 12 | 13 | 14 |
| Part A | | | | |
| Calcium Sulfate | 2.85 | 0 | 0 | 0.85 |
| Calcium Nitrate | 0 | 1.5 | 1.5 | 0 |
| Magnesium Chloride | 0.4 | 0.4 | 0.4 | 0.2 |
| Malic Acid | 0 | 0.95 | 0 | 0 |
| Tartaric Acid | 0 | 0 | 1.05 | 0 |
| Sodium Hydroxide | 0 | 0.575 | 0.575 | 0 |
| Glycerine | 5 | 5 | 5 | 10 |
| Sorbitol | 2.5 | 10 | 10 | 15 |
| Carbowax | 0 | 1 | 1 | 1 |
| CMC | 0.5 | 0.5 | 0.5 | 0.5 |
| Water | 30.4 | 18.725 | 18.625 | 11.15 |
| Methyl Paraben | 0.03 | 0.03 | 0.03 | 0.025 |
| Propyl Paraben | 0.02 | 0.02 | 0.02 | 0.025 |
| Saccharin | 0.3 | 0.3 | 0.3 | 0.25 |
| Zeodent 113 | 4 | 7 | 7 | 7 |
| Zeodent 165 | 2.5 | 2.5 | 2.5 | 2.5 |
| Flavor | 0.5 | 0.5 | 0.5 | 0.5 |
| Tween | 0.5 | 0.5 | 0.5 | 0.5 |
| SLS | 0.5 | 0.5 | 0.5 | 0.5 |
| pH | 7.09 | 6.15 | 6.60 | 6.95 |
| Part B | | | | |
| Glycerine | 5 | 5 | 5 | 10 |
| Sorbitol | 2.5 | 9.81 | 9.81 | 15 |
| Carbowax | 0 | 1 | 1 | 1 |
| CMC | 0.5 | 0.5 | 0.5 | 0.5 |
| Water | 32.2 | 19.69 | 19.69 | 9.55 |
| Sodium Fluoride | 0.25 | 0.25 | 0.25 | 0.25 |
| Monoammonium Phosphate | 1.25 | 2.45 | 2.45 | 2.45 |
| Sodium Saccharin | 0.3 | 0.3 | 0.3 | 0.25 |
| Zeodent 113 | 4 | 7 | 7 | 7 |
| Zeodent 165 | 2.5 | 2.5 | 2.5 | 2.5 |
| Flavor | 0.5 | 0.5 | 0.5 | 0.5 |
| Tween | 0.5 | 0.5 | 0.5 | 0.5 |
| SLS | 0.5 | 0.5 | 0.5 | 0.5 |
| Total | 100 | 100 | 100 | 100 |
| pH | 5.59 | 5.38 | 5.38 | 5.36 |
| pH (A + B) | 5.58 | 5.56 | 5.48 | 5.45 |

TABLE 10

Control Examples E–J: Formulations

| | Concentration (weight percent) Example No. | | | | | |
|---|---|---|---|---|---|---|
| Ingredient | E | F | G | H | I | J |
| Part A | | | | | | |
| Calcium Nitrate | 1 | 0 | 1.5 | 1.5 | 0 | 0 |
| Magnesium Chloride | 0.4 | 0.4 | 0.4 | 0.4 | 0.2 | 0.2 |
| Malonic Acid | 0 | 0 | 0.75 | 0 | 0 | 0 |
| Succinic Acid | 0 | 0 | 0 | 0.85 | 0 | 0 |
| Sodium Hydroxide | 0 | 0 | 0.6 | 0.55 | 0 | 0 |
| Calcium Lactate | 0 | 1 | 0 | 0 | 0 | 1.95 |
| Glycerine | 5 | 5 | 5 | 5 | 10 | 10 |
| Sorbitol | 2.5 | 2.5 | 10 | 10 | 15 | 15 |
| Carbowax | 0 | 0 | 1 | 1 | 1 | 1 |
| CMC | 0.5 | 0.5 | 0.5 | 0.5 | 0.5 | 0.5 |
| Water | 32.25 | 32.25 | 18.9 | 18.85 | 10.5 | 10.05 |

TABLE 10-continued

Control Examples E–J: Formulations

Concentration (weight percent) Example No.

| Ingredient | E | F | G | H | I | J |
|---|---|---|---|---|---|---|
| Methyl Paraben | 0.03 | 0.03 | 0.03 | 0.03 | 0.03 | 0.025 |
| Propyl Paraben | 0.02 | 0.02 | 0.02 | 0.02 | 0.02 | 0.025 |
| Saccharin | 0.3 | 0.3 | 0.3 | 0.3 | 0.25 | 0.25 |
| Zeodent 113 | 4 | 4 | 7 | 7 | 7 | 7 |
| Zeodent 165 | 2.5 | 2.5 | 2.5 | 2.5 | 2.5 | 2.5 |
| Flavor | 0.5 | 0.5 | 0.5 | 0.5 | 0.5 | 0.5 |
| Tween | 0.5 | 0.5 | 0.5 | 0.5 | 0.5 | 0.5 |
| SLS | 0.5 | 0.5 | 0.5 | 0.5 | 0.5 | 0.5 |
| pH | 6.70 | 6.73 | 6.83 | 6.05 | 6.81 | 6.85 |
| Part B | | | | | | |
| Glycerine | 5 | 5 | 5 | 5 | 10 | 10 |
| Sorbitol | 2.5 | 2.5 | 9.81 | 9.81 | 15 | 15 |
| Carbowax | 0 | 0 | 1 | 1 | 1 | 1 |
| CMC | 0.5 | 0.5 | 0.5 | 0.5 | 0.5 | 0.5 |
| Water | 32.2 | 32.2 | 19.69 | 19.69 | 9.55 | 9.55 |
| Sodium Fluoride | 0.25 | 0.25 | 0.25 | 0.25 | 0.25 | 0.25 |
| Mono-ammonium Phosphate | 1.25 | 1.25 | 2.45 | 2.45 | 2.45 | 2.45 |
| Sodium Saccharin | 0.3 | 0.3 | 0.3 | 0.3 | 0.25 | 0.25 |
| Zeodent 113 | 4 | 4 | 7 | 7 | 7 | 7 |
| Zeodent 165 | 2.5 | 2.5 | 2.5 | 2.5 | 2.5 | 2.5 |
| Flavor | 0.5 | 0.5 | 0.5 | 0.5 | 0.5 | 0.5 |
| Tween | 0.5 | 0.5 | 0.5 | 0.5 | 0.5 | 0.5 |
| SLS | 0.5 | 0.5 | 0.5 | 0.5 | 0.5 | 0.5 |
| Total | 100 | 100 | 100 | 100 | 100 | 100 |
| pH | 5.59 | 5.59 | 5.38 | 5.38 | 5.36 | 5.36 |
| pH (A + B) | 5.6 | 5.68 | 5.83 | 5.68 | 5.4 | 5.52 |

The concentration of dissolved calcium cations in each product was estimated by preparing the products without the Zeodents (hydrated silicas), CMC, flavor, or surfactants, and filtering the resultant solution to remove undissolved or precipitated calcium salts. The concentration of calcium cations was then measured by diluting 5 mls of the solution to 100 mls in water/TISAB containing 2 mls of 4M potassium chloride ionic strength adjuster and comparing the calcium electrode response with standards. The concentration of dissolved calcium was then calculated as parts of calcium cations per million parts of the complete toothpaste formulation. The concentration of free fluoride anions in the formulations was measured using the same procedure described hereinabove in connection with Example 8. The concentrations of dissolved calcium cations and undissolved calcium salt in the products of Examples 11–14 and Control Examples E–J are presented in Table 11, while the free fluoride levels and % fluoride lost are presented in Table 12. The ppm recited in Table 11 and the ppm and weight percentages recited in Table 12 are based on the combined weights of the two parts.

TABLE 11

Examples 11–14 and Control Examples E–J: Dissolved/Undissolved Calcium Content of Part A

| Example No. | Dissolved Calcium Cations (ppm) | Undissolved Calcium Salt (ppm) |
|---|---|---|
| 11 | 510 | 7872 |
| 12 | 552 | 1990 |
| 13 | 83 | 2459 |
| 14 | 452 | 2048 |
| E | 1488 | 207 |
| F | 1123 | 176 |
| G | 852 | 1690 |
| H | 1743 | 709 |
| I | 2253 | 199 |
| J | 1893 | 639 |

TABLE 12

Examples 11–14 and E–J: Free Fluoride Levels

| Example No. | Free Fluoride (ppm) | % of Fluoride Lost |
|---|---|---|
| 11 | 1088 | 4 |
| 12 | 940 | 17 |
| 13 | 1182 | 0 |
| 14 | 1219 | 0 |
| E | 459 | 59 |
| F | 829 | 27 |
| G | 876 | 22 |
| H | 754 | 33 |
| I | 374 | 67 |
| J | 655 | 42 |

The results set forth in Table 12 show that if the calcium cation concentration in the liquid part of the calcium-containing portion of the toothpaste (i.e., part A) is limited in this way to no more than about 700 ppm per 50 parts by weight of part A (i.e., no more than about 0.14% by weight of part A), more than 80% by weight of the fluoride ions remains free after mixing the two parts of the toothpaste. In contrast, those formulations in which the calcium cation concentration in the liquid part of the calcium-containing portion of the toothpaste was above above 700 ppm per 50 parts by weight of part A (i.e., more than about 0.14% by weight of part A), the quantity of free fluoride ions can drop to undesirable levels.

Thus, the formulations within the scope of the present invention each lost less than 25% of their fluoride content whereas the formulations in Control Examples E, F, H, I and J lost more than 25%. The Control G formulation, which used the partially water-soluble calcium malonate as its calcium source, also lost less than 25% of its fluoride content.

EXAMPLES 15–18

Examples 15–18 illustrate additional two-part products within the scope of the present invention. The complete formulations of the products in Examples 15–18 are presented in Table 13 below. The weight percentages recited in Table 13 are based on the combined weight of the two parts.

TABLE 13

Examples 15–18: Formulations

| Ingredient | Concentration (weight percent) Example No. | | | |
|---|---|---|---|---|
| | 15 | 16 | 17 | 18 |
| Part (A) | | | | |
| Calcium Sulfate | 0.4 | 0 | 0 | 0.7 |
| Calcium Nitrate | 0 | 0 | 3 | 0 |
| Magnesium Chloride | 0.1 | 0.2 | 0.4 | 0.4 |
| Malic Acid | 0 | 0 | 1.9 | 0 |
| Calcium Malonate | 0 | 2.5 | 0 | 0 |
| Sodium Hydroxide | 0 | 0 | 1.15 | 0 |
| Glycerine | 12 | 25 | 6 | 5 |
| Sorbitol | 12 | 0 | 15 | 16 |
| Carbowax | 1 | 0 | 2 | 2 |
| CMC | 0.5 | 0.5 | 0.5 | 0.5 |
| Water | 11.65 | 12.14 | 9 | 14 |
| Methyl Paraben | 0.02 | 0.02 | 0.02 | 0.02 |
| Propyl Paraben | 0.03 | 0.04 | 0.03 | 0.03 |
| Saccharin | 0.3 | 0.4 | 0.5 | 0.5 |
| Zeodent 113 | 8 | 6 | 7 | 7 |
| Zeodent 165 | 2.5 | 2 | 2.3 | 2.65 |
| Flavor | 0.5 | 0.4 | 0.5 | 0.5 |
| Tween | 0.5 | 0.5 | 0.3 | 0.3 |
| SLS | 0.5 | 0.3 | 0.4 | 0.4 |
| Part B | | | | |
| Glycerine | 12 | 25 | 5 | 5 |
| Sorbitol | 12 | 0 | 20 | 18 |
| Carbowax | 1 | 0 | 2 | 2 |
| CMC | 0.5 | 0.5 | 0.5 | 0.5 |
| Water | 10.5 | 12.15 | 9.45 | 9.64 |
| Sodium Fluoride | 0.25 | 0.25 | 0.25 | 0 |
| Sodium Mono-fluorophosphate | 0 | 0 | 0 | 0.76 |
| Monoammonium Phosphate | 2.45 | 2 | 1.5 | 0 |
| Monopotassium phosphate | 0 | 0 | 0 | 2.8 |
| Sodium Saccharin | 0.3 | 0.3 | 0.3 | 0.3 |
| Zeodent 113 | 7 | 6 | 7 | 7 |
| Zeodent 165 | 2.5 | 2 | 2.5 | 2.5 |
| Flavor | 0.5 | 0.5 | 0.5 | 0.5 |
| Tween | 0.5 | 0.5 | 0.5 | 0.5 |
| SLS | 0.5 | 0.8 | 0.5 | 0.5 |
| Total | 100 | 100 | 100 | 100 |

The concentrations of dissolved calcium cations and undissolved calcium salt in the products of Examples 15 and 16 are measured using the same procedure described hereinabove in connection with Examples 11–14 and Control Examples E–J.

The product of Example 15 contains about 0.05% by weight of dissolved calcium cations and about 0.065% by weight of undissolved calcium salt in the form of calcium sulfate.

In Example 16, the source of calcium is calcium malonate. Although Control Example G herein also contained calcium malonate (malonic acid plus calcium nitrate), such calcium salt provided part A with more than 0.14% by weight calcium cations in the dissolved state. In Example 16, the dissolved calcium content in part A is made to be less than 0.14% by weight by reducing the water content, eliminating the sorbitol and increasing the glycerin content.

The formulation prepared in Example 17 is another calcium-malate based formulation with a lower phosphate content.

In Example 18, the fluoride source is sodium monofluorophosphate.

EXAMPLES 19–22

Examples 19–22 illustrate products within the scope of the present invention which use mixed aqueous/non-aqueous systems. In Part A of the formulations, the calcium salt is suspended in a non-aqueous medium, i.e., Carbowax 400 (polyethylene oxide of molecular weight 400). The products are thickened with Carbowax 8000 (polyethylene oxide of molecular weight 8000) and, in some cases, with Aerosil 200VS silica. Part B of each formulation is aqueous-based. The complete formulations are prepared in two parts and are packaged without a barrier. The non-aqueous portion of the product is provided in the form of stripes on the outside of the aqueous portion of the product. The need for a barrier is eliminated because the calcium-containing part is present in a non-aqueous base and there is virtually no diffusion of the undissolved calcium from the non-aqueous side into the aqueous side and essentially no fluoride diffusion into the non-aqueous part. Thus, the product remains stable until used. The specific formulations of the products prepared in Examples 19–22 are presented in Table 14 below. The weight percentages recited in Table 14 are based on the combined weight of the two parts.

TABLE 14

Examples 19–22: Formulations

| Ingredient | Concentration (weight percent) Example No. | | | |
|---|---|---|---|---|
| | 19 | 20 | 21 | 22 |
| Part A | | | | |
| Carbowax 8000 | 0.80 | 1.20 | 0.70 | 0.80 |
| Aerosil 200VS | 0.20 | 0.00 | 0.00 | 0.20 |
| Carbowax 400 | 5.60 | 6.25 | 4.35 | 5.75 |
| Calcium Sulfate | 2.80 | 0.00 | 2.10 | 0.00 |
| Calcium Malate | 0.00 | 2.00 | 0.00 | 0.00 |
| Calcium Malonate | 0.00 | 0.00 | 0.00 | 3.00 |
| Magnesium Chloride | 0.40 | 0.40 | 0.20 | 0.10 |
| Flavor | 0.15 | 0.10 | 0.10 | 0.10 |
| Saccharin | 0.05 | 0.05 | 0.04 | 0.04 |
| Titanium Dioxide | 0.00 | 0.00 | 0.01 | 0.01 |
| Dye | Trace | Trace | Trace | Trace |
| Part B | | | | |
| Potassium Nitrate | 0.00 | 0.00 | 5.00 | 0.00 |
| Potassium Sulfate | 0.00 | 0.00 | 1.00 | 0.00 |
| Water | 37.30 | 25.85 | 21.15 | 24.75 |
| Sodium Fluoride | 0.25 | 0.25 | 0.25 | 0.25 |
| Monoammonium Phosphate | 2.25 | 5.40 | 0.00 | 0.00 |
| Monopotassium Phosphate | 0.00 | 0.00 | 5.60 | 0.00 |
| Dipotassium Phosphate | 0.00 | 0.00 | 0.00 | 3.00 |
| Tripotassium Phosphate | 0.00 | 0.00 | 0.00 | 3.00 |
| Glycerine | 9.00 | 25.00 | 25.00 | 25.00 |
| Sorbitol | 18.00 | 10.00 | 10.00 | 10.00 |
| PEG 8 | 1.80 | 2.00 | 2.00 | 2.00 |
| Sodium Saccharin | 0.60 | 0.60 | 0.60 | 0.60 |
| CMC | 0.90 | 0.90 | 0.90 | 0.90 |
| Zeodent 113 | 12.40 | 12.30 | 13.30 | 13.00 |
| Zeodent 165 | 4.50 | 4.50 | 4.50 | 4.50 |
| Titanium Dioxide | 0.20 | 0.20 | 0.20 | 0.00 |
| Sodium Lauryl Sulfate | 1.00 | 1.00 | 1.00 | 1.00 |
| Flavor | 0.90 | 1.00 | 1.00 | 1.00 |
| Tween | 0.90 | 1.00 | 1.00 | 1.00 |
| Total | 100.00 | 100.00 | 100.00 | 100.00 |

As shown in Table 14, potassium nitrate is added to part B of the formulation of Example 21 as a desensitizing agent, and 1% potassium sulfate is added to further suppress the solubility of the calcium sulfate and maintain the stability of the formulation when the two parts are mixed in the mouth.

It is believed that when parts A and B in the products Examples 19–22 are mixed, the solubility of the calcium will be sufficient to promote remineralization but insufficient to undesirably precipitate out excessive levels of fluoride.

EXAMPLE 23 and

Control Example K

Example 23 and Control Example K illustrate the impact which the principle "common ion effect" can have on the solubility of the calcium salt.

In Example 23 and Control Example K, two toothpaste products were prepared. Each toothpaste contained calcium sulfate as the calcium source. In addition, each toothpaste contained the FDA-accepted desensitizing agent potassium fluoride at a concentration of about 5%. The potassium fluoride appeared to increase the solubility of the calcium salt in both products. Sodium sulfate (1% by weight) was included in the toothpaste of Example 23 but not in the toothpaste of Control Example K.

Free fluoride analysis of the two toothpaste products was carried out in accordance with the procedure set forth in Example 8 herein. Free fluoride analysis of the toothpaste of Control Example K showed a level of 645 ppm fluoride, indicating a free fluoride loss of about 43%. However, free fluoride analysis of the Example 23 toothpaste showed a free fluoride content of 936 ppm, which indicates a free fluoride loss of only about 17%. Thus, the presence of the common sulfate ion in the Example 23 toothpaste appeared to reduce the solubility of the calcium sulfate therein.

Thus, the foregoing examples show that the products of this invention remineralize subsurface lesions and mineralize exposed dentin tubules without prematurely precipitating calcium, phosphate and fluoride ions and without precipitating excessive levels of free fluoride ions.

What is claimed is:

1. A liquid product for remineralizing subsurface lesions and/or for mineralizing exposed dentin tubules in teeth, comprising:
    (a) a cationic component comprising at least one partially water-soluble calcium salt;
    (b) an anionic component comprising at least one water-soluble phosphate salt and at least one water-soluble fluoride salt; and
    (c) a separating means disposed to separate said components (a) and (b),
    wherein said components (a) and (b) have a pH in water such that a mixed aqueous composition formed by mixing said components (a) and (b) with water and/or saliva has a pH of from about 4.0 to about 10.0;
    further wherein said product contains an amount of said calcium salt such that in said mixed aqueous composition a first portion of said calcium salt exists as dissolved calcium cations and a second portion of said calcium salt exists as undissolved calcium salt, said aqueous composition further comprising dissolved phosphate anions released by said phosphate salt and dissolved fluoride anions released by said fluoride salt.

2. A product according to claim 1, wherein said product comprises water, a concentration of dissolved calcium cations released by said calcium salt in said water and a concentration of an undissolved form of said calcium salt.

3. A product according to claim 2, wherein said concentration of dissolved calcium cations is no more than about 0.14% by weight of said cationic component.

4. A product according to claim 1, wherein said product comprises an amount of said calcium salt such that said mixed aqueous composition comprises from about 100 ppm to no more than about 1400 ppm of said dissolved calcium cations and at least about 500 ppm of said undissolved calcium salt.

5. A product according to claim 4, wherein said amount of said calcium salt in said product is such that said mixed aqueous composition comprises from 100 ppm to about 800 ppm of said dissolved calcium cations and at least about 2000 ppm of said undissolved calcium salt.

6. A product according to claim 1, wherein said amount of said calcium salt in said product is such that said mixed aqueous composition comprises from about 100 ppm to no more than about 1400 ppm of said dissolved calcium cations and at least about 500 ppm of said undissolved calcium salt; further wherein said phosphate salt is present in said product in an amount such that said mixed aqueous composition comprises at least about 100 ppm of said phosphate anions; and further wherein said fluoride salt is present in said product in an amount such that said mixed aqueous composition comprises from about 100 ppm to about 5000 ppm of said fluoride anions.

7. A product according to claim 1, wherein said calcium salt in said product is such that said mixed aqueous composition comprises dissolved calcium cations in an amount such as to provide said mixed aqueous composition with a concentration of said dissolved fluoride anions equal to at least about 75% of fluoride anions in said at least one fluoride salt in said product for a period of up to about 1 minute after formation of said mixed aqueous composition.

8. A product according to claim 1, wherein said cationic component further comprises at least one non-toxic, water-soluble salt of a divalent metal other than calcium.

9. A product according to claim 8, wherein said divalent metal is selected from the group consisting of magnesium, tin, strontium, and zinc.

10. A product according to claim 8, wherein said amount of said calcium salt in said product is such that said mixed aqueous composition comprises from about 100 ppm to no more than about 1400 ppm of said dissolved calcium cations and at least about 500 ppm of said undissolved calcium salt; further wherein said phosphate salt is present in said product in an amount such that said mixed aqueous composition comprises at least about 100 ppm of said phosphate anions; further wherein said fluoride salt is present in said product in an amount such that said mixed aqueous composition comprises from about 100 ppm to about 5000 ppm of said fluoride anions; and further wherein said divalent metal salt is present in said product in an amount such that said mixed aqueous composition comprises at least about 100 ppm of said divalent metal cations.

11. A product according to claim 1, wherein said components (a) and (b) have a pH in water such that said mixed aqueous composition has a pH of from greater than about 4.0 to about 7.0.

12. A product according to claim 1, wherein said calcium salt is selected from the group consisting of calcium sulfate, anhydrous calcium sulfate, calcium sulfate hemihydrate, calcium sulfate dihydrate, calcium dl-malate trihydrate, calcium tartrate, calcium malonate and calcium succinate.

13. A product according to claim 1, wherein said calcium salt is calcium sulfate.

14. A product according to claim 1, wherein said cationic component further comprises a water-soluble salt of a metal other than calcium, wherein said metal salt comprises an anion which is identical to an anion of said calcium salt.

15. A product according to claim 1, wherein said product is a toothpaste, a gel, a professional gel, a dental cream, a mouthwash or a mouth rinse.

16. A product according to claim 1, wherein said product is a two-part product comprising:
(A) a first discrete part containing said cationic component, wherein said cationic component is a liquid;
(B) a second discrete part containing said anionic component, wherein said anionic component is a liquid;
(C) a physical barrier as said separating means, said physical barrier separating said first and second discrete parts; and
(D) a dispensing means for dispensing said cationic liquid component and said anionic liquid component from said two-part product;
wherein said mixed aqueous composition is formed by dispensing said cationic and anionic liquid components from said product and mixing said dispensed anionic and cationic liquid components together with water and/or saliva.

17. A product according to claim 16, wherein either or both of said cationic and anionic liquid components is aqueous.

18. A product according to claim 17, wherein said cationic liquid component is aqueous and comprises no more than about 0.14% by weight of dissolved calcium cations released by said calcium salt and at least about 0.05% by weight of an undissolved form of said calcium salt.

19. A product according to claim 18, wherein said aqueous cationic component comprises no more than about 0.08% by weight of said dissolved calcium cations and at least about 0.20% by weight of said undissolved form of said calcium salt.

20. A product according to claim 18, wherein said aqueous cationic component comprises from about 0.01% to about 0.05% by weight of said dissolved calcium cations and from about 0.20% to about 0.30% by weight of said undissolved form of said calcium salt.

21. A product according to claim 18, wherein said cationic aqueous component further comprises divalent metal cations released by at least one salt of a divalent metal other than calcium.

22. A product according to claim 16, wherein said anionic liquid component is aqueous and comprises dissolved phosphate anions released by said phosphate salt and a first concentration of dissolved fluoride anions released by said fluoride salt.

23. A product according to claim 22, wherein said calcium salt in said product is such as to provide said mixed aqueous composition with a concentration of said dissolved calcium cations which is such as to provide said mixed aqueous composition with a second concentration of said dissolved fluoride anions which is equal to at least about 75% of said first concentration of said dissolved fluoride anions for a period of up to about 1 minute after initial formation of said mixed aqueous composition.

24. A product according to claim 22, wherein said cationic component is aqueous, and said cationic aqueous component and said anionic aqueous component each have a pH such that said mixed aqueous composition has a pH of from greater than about 4.0 to about 7.0.

25. A product according to claim 16, wherein said calcium salt is selected from the group consisting of calcium sulfate, anhydrous calcium sulfate, calcium sulfate hemihydrate, calcium sulfate dihydrate, calcium dl-malate trihydrate, calcium tartrate, calcium malonate and calcium succinate.

26. A product according to claim 16, wherein said calcium salt is calcium sulfate.

27. A product according to claim 16, wherein said dispensing means is adapted to simultaneously dispense said anionic and cationic liquid components from said product.

28. A product according to claim 1, wherein said product is a one-part product comprising a non-aqueous, hydrophilic liquid carrier medium as said separating means, said anionic and cationic components being suspended in said liquid carrier medium, wherein upon mixing of said product with water and/or saliva said liquid carrier medium is capable of releasing said anionic and cationic components into said water and/or saliva so as to form said mixed aqueous composition.

29. A product according to claim 28, wherein said liquid carrier medium is capable of simultaneously releasing said anionic and cationic components into said water and/or saliva.

30. A product according to claim 28, wherein said liquid carrier medium comprises a polyethylene oxide having a molecular weight of about 400.

31. A product according to claim 28, wherein said cationic component further comprises a non-toxic, water-soluble salt of a divalent metal other than calcium.

32. A product according to claim 28, wherein said calcium salt is selected from the group consisting of calcium sulfate, anhydrous calcium sulfate, calcium sulfate hemihydrate, calcium sulfate dihydrate, calcium dl-malate trihydrate, calcium tartrate, calcium malonate and calcium succinate.

33. A product according to claim 28, wherein said calcium salt is calcium sulfate.

34. A mixed aqueous composition for remineralizing subsurface lesions and/or for mineralizing exposed dentin tubules in teeth, comprising:
(a) a concentration of dissolved calcium cations released by at least one partially water-soluble calcium salt;
(b) a concentration of undissolved calcium salt, said undissolved calcium salt being an undissolved form of said partially water-soluble calcium salt;
(c) a concentration of dissolved phosphate anions; and
(d) a concentration of dissolved fluoride anions;
wherein said mixed aqueous composition has a pH of from about 4.0 to about 10.0.

35. A composition according to claim 34, wherein said composition has a pH of from greater than about 4.0 to about 7.0.

36. A composition according to claim 34, wherein said composition has a pH of from about 4.5 to about 6.5.

37. A composition according to claim 34, wherein said mixed aqueous composition comprises from about 100 ppm to no more than about 1400 ppm of said dissolved calcium cations; at least about 500 ppm of said undissolved calcium salt; at least about 100 ppm of said dissolved phosphate anions; and from about 100 ppm to about 5000 ppm of said dissolved fluoride anions.

38. A composition according to claim 34, further comprising a concentration of dissolved divalent metal cations other than calcium cations.

39. A composition according to claim 38, wherein said mixed aqueous composition comprises from about 100 ppm to no more than about 1400 ppm of said dissolved calcium cations; at least about 500 ppm of said undissolved calcium salt; at least about 100 ppm of said dissolved phosphate anions; from about 100 ppm to about 5000 ppm of said dissolved fluoride anions; and at least about 100 ppm of said dissolved divalent metal cations.

40. A two-part packaged product comprising:
(i) a first discrete part comprising a cationic liquid component containing at least one partially water-soluble calcium salt;

(ii) a second discrete part containing an anionic liquid component containing at least one water-soluble phosphate salt and at least one water-soluble fluoride salt; wherein said cationic and anionic liquid components have a pH in water such that a mixed aqueous composition formed by mixing said cationic and anionic components with water and/or saliva has a pH of from about 4.0 to about 10.0; further wherein said product contains an amount of said calcium salt such that in said mixed aqueous composition a first portion of said calcium salt exists as dissolved calcium cations and a second portion of said calcium salt exists as undissolved calcium salt, said aqueous composition further comprising phosphate anions released by said phosphate salt and fluoride anions released by said fluoride salt;

(iii) a dispensing container containing a first discrete compartment and a second discrete compartment each with an outlet end, wherein the first compartment stores the first discrete part and the second compartment stores the second discrete part;

(iv) a closure mechanism for closing the first compartment and the second compartment; and (v) a dispensing means for simultaneously dispensing the cationic liquid component and the anionic liquid component from the product.

41. A method of remineralizing at least one lesion formed in a subsurface of at least one tooth and/or mineralizing at least one exposed tubule in a dentin portion of at least one tooth, comprising the steps of:

(1) providing an mixed aqueous composition having a pH of from about 4.0 to about 10.0 and comprising:
  (a) a concentration of dissolved calcium cations released by at least one partially water-soluble calcium salt;
  (b) a concentration of undissolved calcium salt, said undissolved calcium salt being an undissolved form of said partially water-soluble calcium salt;
  (c) a concentration of dissolved phosphate anions; and
  (d) a concentration of dissolved fluoride anions; and (2) applying said mixed aqueous composition to said at least one tooth for a period of time sufficient to allow diffusion of said calcium cations, said phosphate anions and said fluoride anions through a surface of said tooth to said subsurface and/or to said dentin portion, said cations and anions precipitating at said subsurface to form an insoluble salt on said lesion so as to remineralize said lesion, and/or precipitating at said dentin portion to form an insoluble salt on said exposed tubule so as to mineralize said tubule.

42. A method according to claim 41, wherein said mixed aqueous composition further comprises a concentration of dissolved divalent metal cations other than calcium cations.

43. A method according to claim 41, wherein said step of providing said mixed aqueous composition composition comprises:

(i) providing a liquid product comprising:
  (a) a cationic component comprising at least one partially water-soluble calcium salt;
  (b) an anionic component comprising at least one water-soluble phosphate salt and at least one water-soluble fluoride salt; and
  (c) a separating means disposed to separate said components (a) and (b),
  wherein said components (a) and (b) have a pH in water such that a mixed aqueous composition formed by mixing said components (a) and (b) with water and/or saliva has a pH of from about 4.0 to about 10.0;
  further wherein said product contains an amount of said calcium salt such that in said mixed aqueous composition a first portion of said calcium salt exists as dissolved calcium cations and a second portion of said calcium salt exists as undissolved calcium salt, said aqueous composition further comprising phosphate anions released by said phosphate salt and fluoride anions released by said fluoride salt;

(ii) dispensing said cationic and anionic components from said product; and (iii) mixing said dispensed cationic and anionic components with water and/or saliva so as to form said mixed aqueous composition.

44. A method according to claim 41, wherein said step of providing said mixed aqueous composition comprises:

(i) providing a two-part liquid product comprising:
  (A) a first discrete part containing a liquid cationic component comprising said at least one partially water-soluble calcium salt;
  (B) a second discrete part containing a liquid anionic component comprising at least one water-soluble phosphate salt which releases said phosphate anions and at least one water-soluble fluoride salt which releases said fluoride anions;
  (C) a physical barrier as said separating means, said physical barrier separating said first and second discrete parts; and
  (D) a dispensing means for dispensing said cationic liquid component and said anionic liquid component from said two-part product;

(ii) dispensing said cationic and anionic liquid components from said product; and (iii) mixing said dispensed anionic and cationic liquid components together with water and/or saliva to form said mixed aqueous composition.

* * * * *